(12) United States Patent
Cassayre et al.

(10) Patent No.: US 9,510,595 B2
(45) Date of Patent: Dec. 6, 2016

(54) PESTICIDAL MIXTURES

(71) Applicant: Syngenta Participations AG, Basel (CH)

(72) Inventors: Jerome Yves Cassayre, Stein (CH); Myriem El Qacemi, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/432,296

(22) PCT Filed: Oct. 9, 2013

(86) PCT No.: PCT/EP2013/071061
§ 371 (c)(1),
(2) Date: Mar. 30, 2015

(87) PCT Pub. No.: WO2014/056985
PCT Pub. Date: Apr. 17, 2014

(65) Prior Publication Data
US 2015/0257386 A1    Sep. 17, 2015

(30) Foreign Application Priority Data
Oct. 10, 2012 (EP) .................................... 12187999

(51) Int. Cl.
| | | |
|---|---|---|
| A01N 43/40 | (2006.01) | |
| A01N 43/66 | (2006.01) | |
| A01N 43/82 | (2006.01) | |
| A01N 37/34 | (2006.01) | |
| A01N 43/38 | (2006.01) | |
| A01N 43/56 | (2006.01) | |

(52) U.S. Cl.
CPC ............ *A01N 43/66* (2013.01); *A01N 37/34* (2013.01); *A01N 43/38* (2013.01); *A01N 43/56* (2013.01); *A01N 43/82* (2013.01)

(58) Field of Classification Search
CPC ..................................................... A01N 43/66
USPC ............................................................ 514/341
See application file for complete search history.

(56) References Cited

FOREIGN PATENT DOCUMENTS

| EP | 2230230 A1 | 9/2010 | | |
|---|---|---|---|---|
| EP | WO 2011154433 | * | 5/2011 | ............... A01P 7/04 |
| WO | WO 2008150393 | * | 11/2008 | ......... C07D 413/110 |
| WO | 2011/104087 A1 | | 9/2011 | |
| WO | 2011/154433 A2 | | 12/2011 | |
| WO | 2012/080415 A1 | | 6/2012 | |

OTHER PUBLICATIONS

International Search Report for International Patent Application No. PCT/EP2013/071061 mailed Nov. 20, 2013.

* cited by examiner

*Primary Examiner* — Nizal Chandrakumar
(74) *Attorney, Agent, or Firm* — R. Kody Jones

(57) ABSTRACT

The present invention relates to pesticidal mixtures comprising a component A and a component B, wherein component A is a compound of formula (I) R2 is group X wherein A is A1 or A2 and $X^1$, $X^2$, $X^3$, $B^1$, $B^2$, $B^3$, $Y^1$, $Y^2$, $Y^3$, Z, k, $R^1$ and $R^5$ are as defined in claim 1 and component B is an insecticide. The present invention also relates to methods of using said mixtures for the control of plant pests.

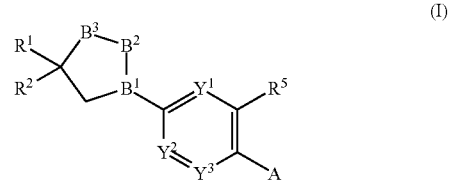

(I)

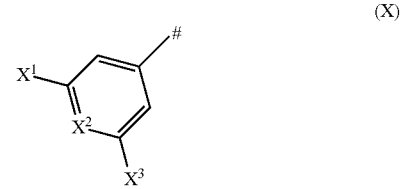

(X)

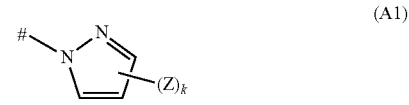

(A1)

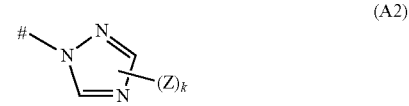

(A2)

9 Claims, No Drawings

PESTICIDAL MIXTURES

RELATED APPLICATION INFORMATION

This application is a 371 of International Application No. PCT/EP2013/071061, filed 9 Oct. 2013, which claims priority to EP Patent Application No. 12187999.3, filed 10 Oct. 2012, the contents of which are incorporated herein by reference herein.

The present invention relates to mixtures of pesticidally active ingredients and to methods of using the mixtures in the field of agriculture.

The present invention provides pesticidal mixtures comprising a component A and a component B, wherein component A is a compound of formula I

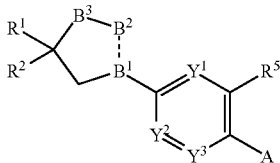

wherein
—$B^1$—$B^2$—$B^3$— is —C=N—O—, —C=N—CH$_2$—, or —N—CH$_2$—CH$_2$—;
$R^1$ is trifluoromethyl, difluoromethyl or chlorodifluoromethyl;
$R^2$ is group X

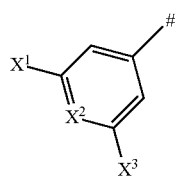

$X^2$ is C—$X^6$ or nitrogen;
$X^1$, $X^3$ and $X^6$ are independently hydrogen, halogen or trihalomethyl, wherein at least one of $X^1$, $X^3$ and $X^6$ is not hydrogen;
A is A1 or A2

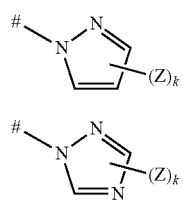

$Y^1$ is C—$R^6$, CH or nitrogen;
$Y^2$ and $Y^3$ are independently CH or nitrogen;
wherein no more than two of $Y^1$, $Y^2$ and $Y^3$ are nitrogen and wherein $Y^2$ and $Y^3$ are not both nitrogen;
$R^5$ is hydrogen, halogen, cyano, nitro, NH$_2$, C$_1$-C$_4$alkyl, C$_1$-C$_4$haloalkyl, C$_3$-C$_5$cycloalkyl, C$_3$-C$_5$halocycloalkyl, C$_1$-C$_2$alkoxy, or C$_1$-C$_2$haloalkoxy;
$R^6$ when present together with $R^5$ forms a —CH=CH—CH=CH— bridge;
each Z is independently halogen, C$_1$-C$_{12}$alkyl or C$_1$-C$_{12}$alkyl substituted by one to five R$^{12}$, nitro, C$_1$-C$_{12}$alkoxy or C$_1$-C$_{12}$alkoxy substituted by one to five R$^{12}$, cyano, C$_1$-C$_{12}$alkylsulfinyl, C$_1$-C$_{12}$alkylsulfonyl, C$_1$-C$_{12}$haloalkylsulfinyl, C$_1$-C$_{12}$haloalkylsulfonyl, hydroxyl or thiol;
each R$^{12}$ is halogen, cyano, nitro, hydroxy, C$_1$-C$_8$alkoxy-, C$_1$-C$_8$haloalkoxy-, mercapto, C$_1$-C$_8$alkylthio-, or C$_1$-C$_8$haloalkylthio; and
k is 0, 1, 2 or 3;
and component B is a compound selected from a) a pyrethroid including those selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

b) an organophosphate including those selected from the group consisting of sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate and diazinon;

c) a carbamate including those selected from the group consisting of pirimicarb, triazamate, cloethocarb, carbofuran, furathiocarb, ethiofencarb, aldicarb, thiofurox, carbosulfan, bendiocarb, fenobucarb, propoxur, methomyl, thiodicarb and oxamyl;

d) a benzoyl urea including those selected from the group consisting of diflubenzuron, triflumuron, hexaflumuron, flufenoxuron, lufenuron and chlorfluazuron;

e) an organic tin compound selected from the group consisting of cyhexatin, fenbutatin oxide and azocyclotin;

f) a pyrazole including those selected from the group consisting of tebufenpyrad and fenpyroximate;

g) a macrolide including those selected from the group consisting of abamectin, emamectin (e.g. emamectin benzoate), ivermectin, milbemycin, spinosad, azadirachtin and spinetoram;

h) an organochlorine compound including those selected from the group consisting of endosulfan (in particular alpha-endosulfan), benzene hexachloride, DDT, chlordane and dieldrin;

i) an amidine including those selected from the group consisting of chlordimeform and amitraz;

j) a fumigant agent including those selected from the group consisting of chloropicrin, dichloropropane, methyl bromide and metam;

k) a neonicotinoid compound including those selected from the group consisting of imidacloprid, thiacloprid, acetamiprid, nitenpyram, dinotefuran, thiamethoxam, clothianidin, nithiazine and flonicamid;

l) a diacylhydrazine including those selected from the group consisting of tebufenozide, chromafenozide and methoxyfenozide;

m) a diphenyl ether including those selected from the group consisting of diofenolan and pyriproxyfen;

n) indoxacarb;

o) chlorfenapyr;

p) pymetrozine;

q) a tetramic acid compound including those selected from the group consisting of spirotetramat and spirodiclofen, or a tetronic acid compound including spiromesifen;
r) a diamide including those selected from the group consisting of flubendiamide, chlorantraniliprole (Rynaxypyr®) and cyantraniliprole;
s) sulfoxaflor;
t) metaflumizone;
u) fipronil and ethiprole;
v) pyrifluqinazon;
w) buprofezin;
x) diafenthiuron;
y) 4-[(6-Chloro-pyridin-3-ylmethyl)-(2,2-difluoro-ethyl)-amino]-5H-furan-2-one;
z) flupyradifurone.

Compounds in ground a)-z) are insecticidal compounds. In addition, component B may be a nematicidally active biological agent. The nematicidally active biological agent refers to any biological agent that has nematicidal activity. The biological agent can be any type known in the art including bacteria and fungi. The wording "nematicidally active" refers to having an effect on, such as reduction in damage caused by, agricultural-related nematodes. The nematicidally active biological agent can be a bacterium or a fungus. Preferably, the biological agent is a bacterium. Examples of nematicidally active bacteria include *Bacillus firmus, Bacillus cereus, Bacillus subtilis, P. nishizawae* and *Pasteuria penetrans*. A suitable *Bacillus firmus* strain is strain CNCM I-1582 which is commercially available as BioNem™. A suitable *Bacillus cereus* strain is strain CNCM I-1562. Of both *Bacillus* strains more details can be found in U.S. Pat. No. 6,406,690. Also of interest are *Streptomyces* spp. such as *S. avermitilis*, and fungi including *Metarhizium* spp. such as *M. anisopliae; Pochonia* spp. such as *P. chlamydosporia.*

Compounds of formula I are known to have insecticidal activity. Certain active ingredient mixtures of a compound of formula I and additional active ingredients can enhance the spectrum of action with respect to the pest to be controlled. For example, the combination of A and B may cause an increase in the expected insecticidal action. This allows, on the one hand, a substantial broadening of the spectrum of pests that can be controlled and, on the other hand, increased safety in use through lower rates of application.

However, besides the actual synergistic action with respect to pest control, the pesticidal compositions according to the invention can have further surprising advantageous properties which can also be described, in a wider sense, as synergistic activity. Examples of such advantageous properties that may be mentioned are: a broadening of the spectrum of pest control to other pests, for example to resistant strains; a reduction in the rate of application of the active ingredients; adequate pest control with the aid of the compositions according to the invention, even at a rate of application at which the individual compounds are totally ineffective; advantageous behaviour during formulation and/ or upon application, for example upon grinding, sieving, emulsifying, dissolving or dispensing; increased storage stability; improved stability to light; more advantageous degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

Compounds of formula I may be prepared according to the methods described WO09097992, WO09072621. The components B are known, e.g. from "The Pesticide Manual", Fifteenth Edition, Edited by Clive Tomlin, British Crop Protection Council.

The combinations according to the invention may also comprise more than one of the active components B, if, for example, a broadening of the spectrum of pest control is desired. For instance, it may be advantageous in the agricultural practice to combine two or three components B with any of the compounds of formula I, or with any preferred member of the group of compounds of formula I. The mixtures of the invention may also comprise other active ingredients in addition to components A and B. In other embodiments the mixtures of the invention may include only components A and B as pesticidally active ingredients, e.g. no more than two pesticidally active ingredients.

The compounds of formula (I) may exist in different geometric or optical isomers or tautomeric forms. This invention covers all such isomers and tautomers and mixtures thereof in all proportions as well as isotopic forms such as deuterated compounds. The invention also covers salts and N-oxides of the compounds of the invention.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Halogen is fluorine, chlorine, bromine or iodine.

Haloalkyl groups are alkyl groups which are substituted by one or more of the same or different halogen atoms and are, for example, difluoromethyl, trifluoromethyl, chlorodifluoromethyl or 2,2,2-trifluoro-ethyl.

The preferences for $B^1$, $B^2$, $B^3$, $R^1$, $R^2$, $Y^1$, $Y^2$, $Y^3$, $R^5$, $R^6$, $R^{12}$, $X^1$, $X^2$, $X^3$, Z and k are, in any combination, as described below.

Preferably $R^1$ is trifluoromethyl, or chlorodifluoromethyl, most preferably trifluoromethyl.

Preferably $X^1$, $X^3$ and $X^6$ are independently hydrogen, halogen or trifluoromethyl, wherein at least two of $X^1$, $X^3$ and $X^6$ are not hydrogen. More preferably $X^1$, $X^3$ and $X^6$ are independently hydrogen, chloro, bromo or trifluoromethyl, wherein at least two of $X^1$, $X^3$ and $X^6$ are not hydrogen. Preferably at least two of $X^1$, $X^3$ and $X^6$ are chloro, bromo or trifluoromethyl. Very preferably $X^2$ is C—$X^6$ and at least two of $X^1$, $X^3$ and $X^6$ are chloro, bromo or trifluoromethyl.

In one group of compounds $R^2$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, 3-bromo-5-(trifluoromethyl)phenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl) phenyl-, 3-(trifluoromethyl)phenyl-, 2,6-dichloro-4- pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably $R^2$ is 3,5-dichloro-phenyl, 3,5-dichloro-4-fluorophenyl- or 3,4,5-trichloro-phenyl, most preferably 3,5-dichloro-phenyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. Most preferably $Y^1$ is CH, $Y^2$ is CH, and $Y^3$ is CH.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, most preferably $R^5$ is hydrogen, cyano, chloro, bromo, fluoro, methyl, or trifluoromethyl, most preferably cyano.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, most preferably each Z is independently hydrogen, cyano, halogen, methyl, halomethyl, methoxy or halomethoxy, most preferably cyano or trifluoromethyl.

Each $R^{12}$ is preferably bromo, chloro, fluoro, methoxy, or methylthio, most preferably chloro, fluoro, or methoxy Preferably k is 0 or 1, more preferably k is 1 when A is A1 (preferably at the 4 position of the pyrazole moiety) and k is 0 when A is A2.

In one group of compounds —$B^1$—$B^2$—$B^3$— is —C=N—O—.

In another group of compounds —$B^1$—$B^2$—$B^3$— is —C=N—CH$_2$—.

In another group of compounds —$B^1$—$B^2$—$B^3$— is —N—CH$_2$—CH$_2$—.

In another group of compounds $Y^1$ is C—$R^6$ and $R^6$ together with $R^5$ forms a —CH=CH—CH=CH— bridge.

In one embodiment the compound of formula I is a compound of formula IA (IA)

wherein $B^1$, $B^2$, $B^3$, $R^1$, $R^2$, $Y^1$, $Y^2$, $Y^3$, $R^5$ Z and k are as defined for a compound of formula I In compounds of formula IA preferred definitions of $B^1$, $B^2$, $B^3$, $R^1$, $R^2$, $Y^1$, $Y^2$, $Y^3$, $R^5$, Z and k are, in any combination, as set out below Preferably $R^1$ is trifluoromethyl, or chlorodifluoromethyl, most preferably trifluoromethyl.

Preferably $X^1$, $X^3$ and $X^6$ are independently hydrogen, halogen or trifluoromethyl, wherein at least two of $X^1$, $X^3$ and $X^6$ are not hydrogen. More preferably $X^1$, $X^3$ and $X^6$ are independently hydrogen, chloro, bromo or trifluoromethyl, wherein at least two of $X^1$, $X^3$ and $X^6$ are not hydrogen. Preferably at least two of $X^1$, $X^3$ and $X^6$ are chloro, bromo or trifluoromethyl, more preferably $X^2$ is C—$X^6$ and at least two of $X^1$, $X^3$ and $X^6$ are chloro, bromo or trifluoromethyl.

In one group of compounds 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, 3-bromo-5-(trifluoromethyl)phenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably $R^2$ is 3,5-dichloro-phenyl, 3,5-dichloro-4-fluorophenyl- or 3,4,5-trichloro-phenyl, most preferably 3,5-dichloro-phenyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. Most preferably $Y^1$ is CH, $Y^2$ is CH, and $Y^3$ is CH.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, even more preferably $R^5$ is hydrogen, cyano, chloro, bromo, fluoro, methyl, or trifluoromethyl, most preferably cyano.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, more preferably each Z is independently hydrogen, cyano, halogen, methyl, halomethyl, methoxy or halomethoxy, most preferably cyano or trifluoromethyl.

Preferably k is 0 or 1, most preferably 0.

In one group of compounds of formula IA —$B^1$—$B^2$—$B^3$— is —C=N—O—.

In another group of compounds of formula IA —$B^1$—$B^2$—$B^3$— is —C=N—O— and $Y^1$ is CH, $Y^2$ is CH, $Y^3$ is CH.

In another group of compounds of formula IA —$B^1$—$B^2$—$B^3$— is —C=N—O—, $Y^1$ is CH, $Y^2$ is CH, $Y^3$ is CH and $R^1$ is CF$_3$.

In another group of compounds of formula IA —$B^1$—$B^2$—$B^3$— is —C=N—O—, $Y^1$ is CH, $Y^2$ is CH, $Y^3$ is CH, $R^1$ is CF$_3$ and $R^5$ is cyano.

In another group of compounds of formula IA —$B^1$—$B^2$—$B^3$— is —C=N—O—, $Y^1$ is CH, $Y^2$ is CH, $Y^3$ is CH, $R^1$ is CF$_3$, and k is 0 or k is 1 and Z is cyano or trifluoromethyl.

In another group of compounds of formula IA —$B^1$—$B^2$—$B^3$— is —C=N—O—, $Y^1$ is CH, $Y^2$ is CH, $Y^3$ is CH, $R^1$ is CF$_3$, $R^5$ is cyano and k is 0 or k is 1 and Z is cyano or trifluoromethyl.

In another group of compounds of formula IA —$B^1$—$B^2$—$B^3$— is —C=N—O—, $Y^1$ is CH, $Y^2$ is CH, $Y^3$ is CH, $R^1$ is CF$_3$, $R^5$ is cyano and k is 0.

In another group of compounds of formula IA —$B^1$—$B^2$—$B^3$— is —C=N—O—, $Y^1$ is CH, $Y^2$ is CH, $Y^3$ is CH, $R^1$ is CF$_3$, $R^5$ is cyano and k is 0 or k is 1 and Z is cyano or trifluoromethyl and $R^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IA —$B^1$—$B^2$—$B^3$— is —C=N—CH$_2$—.

In another group of compounds of formula IA —B$^1$—B$^2$—B$^3$— is —C=N—CH$_2$—, Y$^1$ is CH, Y$^2$ is CH, Y$^3$ is CH.

In another group of compounds of formula IA —B$^1$—B$^2$—B$^3$— is —C=N—CH$_2$—, Y$^1$ is CH, Y$^2$ is CH, Y$^3$ is CH and R$^1$ is CF$_3$.

In another group of compounds of formula IA —B$^1$—B$^2$—B$^3$— is —C=N—CH$_2$—, Y$^1$ is CH, Y$^2$ is CH, Y$^3$ is CH, R$^1$ is CF$_3$ and R$^5$ is cyano.

In another group of compounds of formula IA —B$^1$—B$^2$—B$^3$— is —C=N—CH$_2$—, Y$^1$ is CH, Y$^2$ is CH, Y$^3$ is CH, R$^1$ is CF$_3$, and k is 0 or k is 1 and Z is cyano or trifluoromethyl.

In another group of compounds of formula IA —B$^1$—B$^2$—B$^3$— is —C=N—CH$_2$—, Y$^1$ is CH, Y$^2$ is CH, Y$^3$ is CH, R$^1$ is CF$_3$, R$^5$ is cyano and k is 0 or k is 1 and Z is cyano or trifluoromethyl.

In another group of compounds of formula IA —B$^1$—B$^2$—B$^3$— is —C=N—CH$_2$—, Y$^1$ is CH, Y$^2$ is CH, Y$^3$ is CH, R$^1$ is CF$_3$, R$^5$ is cyano and k is 0.

In another group of compounds of formula IA —B$^1$—B$^2$—B$^3$— is —C=N—CH$_2$—, Y$^1$ is CH, Y$^2$ is CH, Y$^3$ is CH, R$^1$ is CF$_3$, R$^5$ is cyano and k is 0 or k is 1 and Z is cyano or trifluoromethyl and R$^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IA —B$^1$—B$^2$—B$^3$— is —N—CH$_2$—CH$_2$—.

In another group of compounds of formula IA —B$^1$—B$^2$—B$^3$— is —N—CH$_2$—CH$_2$— and Y$^1$ is CH, Y$^2$ is CH, Y$^3$ is CH.

In another group of compounds of formula IA —B$^1$—B$^2$—B$^3$— is —N—CH$_2$—CH$_2$—, Y$^1$ is CH, Y$^2$ is CH, Y$^3$ is CH and R$^1$ is CF$_3$.

In another group of compounds of formula IA —B$^1$—B$^2$—B$^3$— is —N—CH$_2$—CH$_2$—, Y$^1$ is CH, Y$^2$ is CH, Y$^3$ is CH, R$^1$ is CF$_3$ and R$^5$ is cyano.

In another group of compounds of formula IA —B$^1$—B$^2$—B$^3$— is —N—CH$_2$—CH$_2$—, Y$^1$ is CH, Y$^2$ is CH, Y$^3$ is CH, R$^1$ is CF$_3$, and k is 0 or k is 1 and Z is cyano or trifluoromethyl.

In another group of compounds of formula IA —B$^1$—B$^2$—B$^3$— is —N—CH$_2$—CH$_2$—, Y$^1$ is CH, Y$^2$ is CH, Y$^3$ is CH, R$^1$ is CF$_3$, R$^5$ is cyano and k is 0 or k is 1 and Z is cyano or trifluoromethyl.

In another group of compounds of formula IA —B$^1$—B$^2$—B$^3$— is —N—CH$_2$—CH$_2$—, Y$^1$ is CH, Y$^2$ is CH, Y$^3$ is CH, R$^1$ is CF$_3$, R$^5$ is cyano and k is 0.

In another group of compounds of formula IA —B$^1$—B$^2$—B$^3$— is —N—CH$_2$—CH$_2$—, Y$^1$ is CH, Y$^2$ is CH, Y$^3$ is CH, R$^1$ is CF$_3$, R$^5$ is cyano and k is 0 or k is 1 and Z is cyano or trifluoromethyl and R$^2$ is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In another group of compounds of formula IA R$^5$ is cyano, k is 0 or 1 and Z is cyano or trifluoromethyl.

In another group of compounds of formula IA R$^5$ is cyano, R$^1$ is CF$_3$, —B$^1$—B$^2$—B$^3$— is —C=N—O— or —C=N—CH$_2$—, Y$^1$, Y$^2$ and Y$^3$ are CH, and k is 0.

In one embodiment the compound of formula I is a compound of formula IB

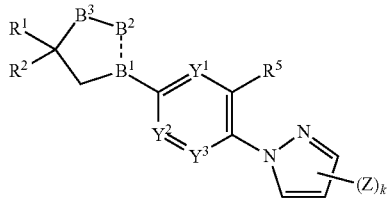

(IB)

wherein B$^1$, B$^2$, B$^3$, R$^1$, R$^2$, Y$^1$, Y$^2$, Y$^3$, R$^5$ Z and k are as defined for a compound of formula I In compounds of formula IB preferred definitions of B$^1$, B$^2$, B$^3$, R$^1$, R$^2$, Y$^1$, Y$^2$, Y$^3$, R$^5$ Z and k are, in any combination, as set out below Preferably R$^1$ is trifluoromethyl, or chlorodifluoromethyl, most preferably trifluoromethyl.

Preferably X$^1$, X$^3$ and X$^6$ are independently hydrogen, halogen or trifluoromethyl, wherein at least two of X$^1$, X$^3$ and X$^6$ are not hydrogen. More preferably X$^1$, X$^3$ and X$^6$ are independently hydrogen, chloro, bromo or trifluoromethyl, wherein at least two of X$^1$, X$^3$ and X$^6$ are not hydrogen. Preferably at least two of X$^1$, X$^3$ and X$^6$ are chloro, bromo or trifluoromethyl, more preferably X$^2$ is C—X$^6$ and at least two of X$^1$, X$^3$ and X$^6$ are chloro, bromo or trifluoromethyl.

In one group of compounds R$^2$ is 3,5-dichlorophenyl-, 3-chloro-4-fluorophenyl-, 3-fluoro-4-chlorophenyl-, 3,4-dichlorophenyl-, 3-chloro-4-bromophenyl-, 3,5-dichloro-4-fluorophenyl-, 3,4,5-trichlorophenyl-, 3,5-dichloro-4-iodophenyl-, 3,4,5-trifluorophenyl-, 3-chloro-5-bromophenyl-, 3-chloro-5-fluorophenyl-, 3-chloro-5-(trifluoromethyl)phenyl-, 3,4-dichloro-5-(trifluoromethyl)phenyl-, 3,5-bis(trifluoromethyl)phenyl-, 4-chloro-3,5-bis(trifluoromethyl)phenyl-, 3-(trifluoromethyl)phenyl-, 2,6-dichloro-4-pyridyl-, 2,6-bis(trifluoromethyl)-4-pyridyl-, 3-bromo-5-(trifluoromethyl)phenyl-, more preferably 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-, more preferably R$^2$ is 3,5-dichloro-phenyl, 3,5-dichloro-4-fluorophenyl- or 3,4,5-trichloro-phenyl, most preferably 3,5-dichloro-phenyl.

Preferably Y$^1$ is CH, Y$^2$ is CH, Y$^3$ is CH, or Y$^1$ is N, Y$^2$ is CH, Y$^3$ is CH, or Y$^1$ is N, Y$^2$ is N, Y$^3$ is CH, or Y$^1$ is CH, Y$^2$ is N, Y$^3$ is CH, or Y$^1$ is CH, Y$^2$ is CH, Y$^3$ is N. Most preferably Y$^1$ is CH, Y$^2$ is CH, and Y$^3$ is CH.

Preferably R$^5$ is hydrogen, chloro, bromo, fluoro, trifluoromethyl, methyl, ethyl, methoxy, nitro, trifluoromethoxy, cyano, cyclopropyl, more preferably R$^5$ is hydrogen, chloro, bromo, fluoro, trifluoromethyl, methyl, ethyl, nitro, cyano, cyclopropyl, even more preferably R$^5$ is hydrogen, cyano, chloro, bromo, fluoro, methyl, or trifluoromethyl, most preferably cyano.

Preferably each Z is independently halogen, cyano, C$_1$-C$_4$alkyl, C$_1$-C$_4$haloalkyl, C$_1$-C$_4$alkoxy, or C$_1$-C$_4$haloalkoxy, more preferably each Z is independently hydrogen, cyano, halogen, methyl, halomethyl, methoxy or halomethoxy, most preferably cyano or trifluoromethyl.

Preferably k is 0 or 1.

In one group of compounds of formula IB —B$^1$—B$^2$—B$^3$— is —C=N—O—.

In another group of compounds of formula IB —B¹—B²—B³— is —C=N—O— and Y¹ is CH, Y² is CH, Y³ is CH.

In another group of compounds of formula IB —B¹—B²—B³— is —C=N—O—, Y¹ is CH, Y² is CH, Y³ is CH and R¹ is CF₃.

In another group of compounds of formula IB —B¹—B²—B³— is —C=N—O—, Y¹ is CH, Y² is CH, Y³ is CH, R¹ is CF₃ and R⁵ is cyano.

In another group of compounds of formula IB —B¹—B²—B³— is —C=N—O—, Y¹ is CH, Y² is CH, Y³ is CH, R¹ is CF₃, and k is 0 or k is 1 and Z is cyano or trifluoromethyl.

In another group of compounds of formula IB —B¹—B²—B³— is —C=N—O—, Y¹ is CH, Y² is CH, Y³ is CH, R¹ is CF₃, R⁵ is cyano and k is 0 or k is 1 and Z is cyano or trifluoromethyl.

In another group of compounds of formula IB —B¹—B²—B³— is —C=N—O—, Y¹ is CH, Y² is CH, Y³ is CH, R¹ is CF₃, R⁵ is cyano and k is 0 or k is 1 and Z is cyano or trifluoromethyl and R² is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IB —B¹—B²—B³— is —C=N—CH₂—.

In another group of compounds of formula IB —B¹—B²—B³— is —C=N—CH₂— and Y¹ is CH, Y² is CH, Y³ is CH.

In another group of compounds of formula IB —B¹—B²—B³— is —C=N—CH₂—, Y¹ is CH, Y² is CH, Y³ is CH and R¹ is CF₃.

In another group of compounds of formula IB —B¹—B²—B³— is —C=N—CH₂—, Y¹ is CH, Y² is CH, Y³ is CH, R¹ is CF₃ and R⁵ is cyano.

In another group of compounds of formula IB —B¹—B²—B³— is —C=N—CH₂—, Y¹ is CH, Y² is CH, Y³ is CH, R¹ is CF₃, and k is 0 or k is 1 and Z is cyano or trifluoromethyl.

In another group of compounds of formula IB —B¹—B²—B³— is —C=N—CH₂—, Y¹ is CH, Y² is CH, Y³ is CH, R¹ is CF₃, R⁵ is cyano and k is 0 or k is 1 and Z is cyano or trifluoromethyl.

In another group of compounds of formula IB —B¹—B²—B³— is —C=N—CH₂—, Y¹ is CH, Y² is CH, Y³ is CH, R¹ is CF₃, R⁵ is cyano and k is 0 or k is 1 and Z is cyano or trifluoromethyl and R² is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In one group of compounds of formula IB —B¹—B²—B³— is —N—CH₂—CH₂—.

In another group of compounds of formula IB —B¹—B²—B³— is —N—CH₂—CH₂— and Y¹ is CH, Y² is CH, Y³ is CH.

In another group of compounds of formula IB —B¹—B²—B³— is —N—CH₂—CH₂—, Y¹ is CH, Y² is CH, Y³ is CH and R¹ is CF₃.

In another group of compounds of formula IB —B¹—B²—B³— is —N—CH₂—CH₂—, Y¹ is CH, Y² is CH, Y³ is CH, R¹ is CF₃ and R⁵ is cyano.

In another group of compounds of formula IB —B¹—B²—B³— is —N—CH₂—CH₂—, Y¹ is CH, Y² is CH, Y³ is CH, R¹ is CF₃, and k is 0 or k is 1 and Z is cyano or trifluoromethyl.

In another group of compounds of formula IB —B¹—B²—B³— is —N—CH₂—CH₂—, Y¹ is CH, Y² is CH, Y³ is CH, R¹ is CF₃, R⁵ is cyano and k is 0 or k is 1 and Z is cyano or trifluoromethyl.

In another group of compounds of formula IB —B¹—B²—B³— is —N—CH₂—CH₂—, Y¹ is CH, Y² is CH, Y³ is CH, R¹ is CF₃, R⁵ is cyano and k is 0 or k is 1 and Z is cyano or trifluoromethyl and R² is 3-chloro-5-bromophenyl-, 3-chloro-5-(trifluoromethyl)phenyl-, 3,5-dichloro-4-fluorophenyl-, 3,4,5-trichlorophenyl-, 3,5-bis(trifluoromethyl)phenyl-, 3-(trifluoromethyl)phenyl-, 2,6-dichloro-4-pyridyl-, 2,6-bis(trifluoromethyl)-4-pyridyl-, 3,5-dichloro-4-bromophenyl-, 3-bromo-5-(trifluoromethyl)phenyl-, 3,5-dibromophenyl-, or 3,4-dichlorophenyl-.

In another group of compounds of formula IB R⁵ is cyano, k is 0 or 1 and Z is cyano or trifluoromethyl.

In another group of compounds of formula IB R⁵ is cyano, k is 0 or 1 and Z is cyano or trifluoromethyl, R¹ is CF₃, —B¹—B²—B³— is —C=N—O— or —C=N—CH₂—, Y¹, Y² and Y³ are CH.

In all embodiments and compounds of formula IB when k is 1 Z is preferably attached at the 4 position of the pyrazole moiety as indicated below

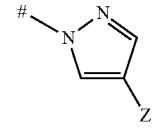

The following compounds of formula I-1, I-2 and I-3 illustrate the compounds of formula I when —B¹—B²—B³— is —C=N—O—, —C=N—CH₂—, or —N—CH₂—CH₂— respectively.

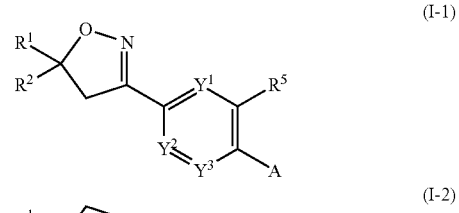

(I-1)

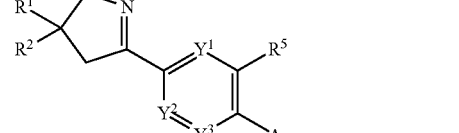

(I-2)

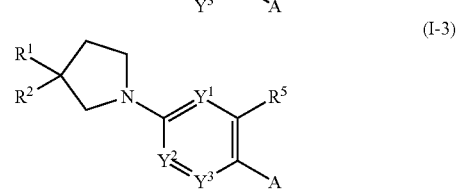

(I-3)

Particularly preferred are compounds of formula IA, wherein —B¹—B²—B³— is —C=N—O— or —C=N—CH₂—, Y¹ is CH, Y² is CH, Y³ is CH and R¹ is CF₃, and in particular wherein R⁵ is cyano. Very particularly preferred are compounds of formula IA wherein —B$^1$—B$^2$—B$^3$— is —C=N—O— or —C=N—CH$_2$—, Y$^1$ is CH, Y$^2$ is CH, Y$^3$ is CH, R$^1$ is CF$_3$, R$^5$ is cyano, k is 0, and in particular wherein X$^2$ is C—X$^6$.

Most preferred are compounds of formula IA wherein —B$^1$—B$^2$—B$^3$— is —C=N—O—, Y$^1$ is CH, Y$^2$ is CH, Y$^3$ is CH, R$^1$ is CF$_3$, R$^5$ is cyano, k is 0, and in particular wherein X$^2$ is C—X$^6$ and at least two of X$^1$, X$^3$ and X$^6$ are chloro, bromo or trifluoromethyl.

Compounds of formula I include at least one chiral centre and may exist as compounds of formula I* or compounds of formula I**. Compounds I* and I** are enantiomers if there is no other chiral center or epimers otherwise.

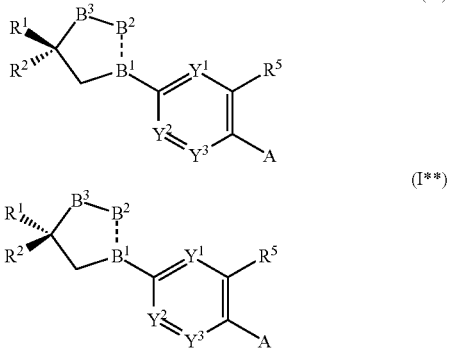

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixtures of formula I*, the molar proportion of the compound of formula I* compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred.

Tables 1 to 9 below illustrate compounds of the invention.

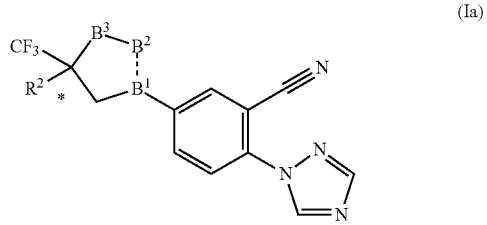

Table 1
Table 1 provides 38 compounds of formula Ia wherein B1-B2-B3 is C=N—O, and R2 is as defined in Table Q.
Table 2
Table 2 provides 38 compounds of formula Ia wherein B1-B2-B3 is C=N—CH2, and R2 is as defined in Table Q.

Table 3
Table 3 provides 38 compounds of formula Ia wherein B1-B2-B3 is N—CH2-CH2, and R2 is as defined in Table Q.

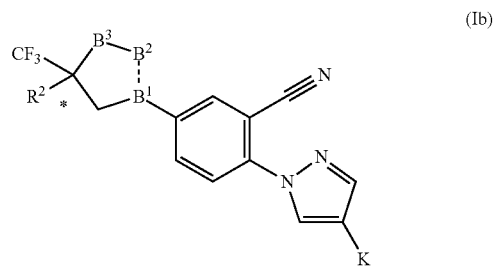

Table 4
Table 4 provides 38 compounds of formula Ib wherein k is CN, B1-B2-B3 is C=N—O and R2 is as defined in Table Q.
Table 5
Table 5 provides 38 compounds of formula Ib wherein k is CF3, B1-B2-B3 is C=N—O and R2 is as defined in Table Q.
Table 6
Table 6 provides 38 compounds of formula Ib wherein k is CN, B1-B2-B3 is C=N—CH2 and R2 is as defined in Table Q.
Table 7
Table 7 provides 38 compounds of formula Ib wherein k is CF3, B1-B2-B3 is C=N—CH2 and R2 is as defined in Table Q.
Table 8
Table 8 provides 38 compounds of formula Ib wherein k is CN, B1-B2-B3 is N—CH2-CH2 and R2 is as defined in Table Q.
Table 9
Table 9 provides 38 compounds of formula Ib wherein k is CF3, B1-B2-B3 is N—CH2-CH2 and R2 is as defined in Table Q.

TABLE Q

| | Stereochemistry at * | R2 |
|---|---|---|
| 1 | Racemic | 3,5-dichlorophenyl |
| 2 | Racemic | 3-chloro-4-fluorophenyl |
| 3 | Racemic | 3-fluoro-4-chlorophenyl |
| 4 | Racemic | 3,4-dichlorophenyl |
| 5 | Racemic | 3-chloro-4-bromophenyl |
| 6 | Racemic | 3,5-dichloro-4-fluorophenyl |
| 7 | Racemic | 3,4,5-trichlorophenyl |
| 8 | Racemic | 3,5-dichloro-4-iodophenyl |
| 9 | Racemic | 3,4,5-trifluorophenyl |
| 10 | Racemic | 3-chloro-5-bromophenyl |
| 11 | Racemic | 3-chloro-5-fluorophenyl |
| 12 | Racemic | 3-chloro-5-(trifluoromethyl)phenyl |
| 13 | Racemic | 3,4-dichloro-5-(trifluoromethyl)phenyl |
| 14 | Racemic | 3,5-bis(trifluoromethyl)phenyl |
| 15 | Racemic | 4-chloro-3,5-bis(trifluoromethyl)phenyl |
| 16 | Racemic | 3-(trifluoromethyl)phenyl |
| 17 | Racemic | 2,6-dichloro-4-pyridyl |
| 18 | Racemic | 2,6-bis(trifluoromethyl)-4-pyridyl |
| 19 | Racemic | 3-bromo-5-(trifluoromethyl)phenyl- |
| 20 | As for compound of formula I** | 3,5-dichlorophenyl |
| 21 | As for compound of formula I** | 3-chloro-4-fluorophenyl |
| 22 | As for compound of formula I** | 3-fluoro-4-chlorophenyl |
| 23 | As for compound of formula I** | 3,4-dichlorophenyl |
| 24 | As for compound of formula I** | 3-chloro-4-bromophenyl |

TABLE Q-continued

| | Stereochemistry at * | R2 |
|---|---|---|
| 25 | As for compound of formula I** | 3,5-dichloro-4-fluorophenyl |
| 26 | As for compound of formula I** | 3,4,5-trichlorophenyl |
| 27 | As for compound of formula I** | 3,5-dichloro-4-iodophenyl |
| 28 | As for compound of formula I** | 3,4,5-trifluorophenyl |
| 29 | As for compound of formula I** | 3-chloro-5-bromophenyl |
| 30 | As for compound of formula I** | 3-chloro-5-fluorophenyl |
| 31 | As for compound of formula I** | 3-chloro-5-(trifluoromethyl)phenyl |
| 32 | As for compound of formula I** | 3,4-dichloro-5-(trifluoromethyl)phenyl |
| 33 | As for compound of formula I** | 3,5-bis(trifluoromethyl)phenyl |
| 34 | As for compound of formula I** | 4-chloro-3,5-bis(trifluoromethyl)phenyl |
| 35 | As for compound of formula I** | 3-(trifluoromethyl)phenyl |
| 36 | As for compound of formula I** | 2,6-dichloro-4-pyridyl |
| 37 | As for compound of formula I** | 2,6-bis(trifluoromethyl)-4-pyridyl |
| 38 | As for compound of formula I** | 3-bromo-5-(trifluoromethyl)phenyl- |

Compound of formula 1-1 and 2-7 are particularly preferred.

In one embodiment of the invention component B is an insecticidal compound selected from the group consisting of neonicotinoids, tetramic acids and tetronic acids, pyrethroids, diamides, carbamates, ethiprole, flupyradifurone, fipronil and -4-[[(6-Chloropyridin-3-yl)methyl](2,2-difluoroethyl)amino]furan-2(5H)-one.

In a further embodiment of the invention component B is an insecticidal compound selected from the group consisting of neonicotinoids, tetramic acids, pyrethroids, diamides and -4-[[(6-Chloropyridin-3-yl)methyl](2,2-difluoroethyl) amino]furan-2(5H)-one.

In a further embodiment of the invention component B is an insecticidal compound selected from the group consisting of neonicotinoids, tetramic acids, and pyrethroids.

In a further embodiment of the invention component B is an insecticidal compound selected from the group consisting of imidacloprid thiacloprid, spirotetramat, spiromesifen, spirodiclofen, flubendiamide, ethiprole, flupyradifurone, thiodicarb, deltamethrin, beta-cyfluthrin, aldicarb, fipronil, 4-[[(6-Chloropyridin-3-yl)methyl](2,2-difluoroethyl) amino]furan-2(5H)-one, lambda-cyhalothrin, and thiamethoxam.

In a further embodiment of the invention component B is an insecticidal compound selected from the group consisting of imidacloprid, thiacloprid, spirotetramat, spirodiclofen, flubendiamide, deltamethrin, beta-cyfluthrin, 4-[[(6-Chloropyridin-3-yl)methyl](2,2-difluoroethyl)amino]furan-2(5H)-one, lambda-cyhalothrin, and thiamethoxam In one embodiment of the invention component B is an insecticidal compound selected from the group consisting of
  pymetrozine;
  an organophosphate selected from the group consisting of sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate and diazinon;
  a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R, 3S)-2,2-dimethyl-3-(2-oxothiolan-3-ylidenemethyl)cyclopropane carboxylate;
  a carbamate including those selected from the group consisting of pirimicarb, triazamate, cloethocarb, carbofuran, furathiocarb, ethiofencarb, aldicarb, thiofurox, carbosulfan, bendiocarb, fenobucarb, propoxur, methomyl, thiodicarb and oxamyl; a macrolide selected from the group consisting of abamectin, emamectin benzoate, ivermectin, milbemycin, spinosad, azadirachtin and spinetoram;
  a diamide selected from the group consisting of flubendiamide, chlorantraniliprole (Rynaxypyr®) and cyantraniliprole;
  a neonicotinoid compound selected from the group consisting of imidacloprid, thiacloprid, acetamiprid, nitenpyram, dinotefuran, thiamethoxam, clothianidin, nithiazine and flonicamid; a tetramic acid or tetronic acid selected from spirotetramat, spirodiclofen and spiromesifen;
  fipronil.

In one embodiment of the invention component B is a compound selected from the group consisting of abamectin, chlorpyrifos, cyantraniliprole, emamectin, lambda cyhalothrin, pymetrozine, spirotetramat, thiamethoxam, clothianidin, imidacloprid and chlorantraniliprole.

In one embodiment of the invention component B is a compound selected from the group consisting of abamectin, chlorpyrifos, cyantraniliprole, emamectin, lambda cyhalothrin, pymetrozine, spirotetramat, and thiamethoxam.

In one embodiment of the invention component B is a compound selected from the group consisting of abamectin, lambda cyhalothrin, spirotetramat and clothianidin.

In one embodiment of the invention component B is a compound selected from the group consisting of spirotetramat, imidacloprid and deltamethrin.

In one embodiment component B is abamectin. In one embodiment component B is lambda cyhalothrin. In one embodiment component B is spirotetramat. In one embodiment component B is clothianidin. In one embodiment component B is imidacloprid. In one embodiment component B is deltamethrin.

In one embodiment of the invention component B is a tetramic acid compound including those selected from spirotetramat and spirodiclofen, e.g. spirotetramat or spirodiclofen, preferably spirotetramat.

In one preferred embodiment of the invention component A is a compound of formula IA, wherein —$B^1$—$B^2$—$B^3$— is —C=N—O—, $Y^1$ is CH, $Y^2$ is CH, $Y^3$ is CH and $R^1$ is $CF_3$, $R^5$ is cyano, A is A2, k is 0 and $X^2$ is C—$X^6$, and component B is a compound as described above, wherein the weight ratio of A to B is 1:250 to 250:1.

In one preferred embodiment of the invention component A is a compound of formula IA, wherein —$B^1$—$B^2$—$B^3$— is —C=N—O—, $Y^1$ is CH, $Y^2$ is CH, $Y^3$ is CH and $R^1$ is $CF_3$, $R^5$ is cyano, A is A2, k is 0 and $X^2$ is C—$X^6$, and component B is a compound as described above, wherein the weight ratio of A to B is 1:25 to 25:1.

In one preferred embodiment of the invention component A is a compound of formula IA, wherein —B$^1$—B$^2$—B$^3$— is —C=N—O—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a compound as described above, wherein the weight ratio of A to B is 1:5 to 5:1.

In one preferred embodiment of the invention component A is a compound of formula IA, wherein —B$^1$—B$^2$—B$^3$— is —C=N—O—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is tetramic acid compound including those selected from spirotetramat and spirodiclofen, wherein the weight ratio of A to B is 1:250 to 250:1.

In one preferred embodiment of the invention component A is a compound of formula IA, wherein —B$^1$—B$^2$—B$^3$— is —C=N—O—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a tetramic acid compound including those selected from spirotetramat and spirodiclofen, wherein the weight ratio of A to B is 1:25 to 25:1.

In one preferred embodiment of the invention component A is a compound of formula IA, wherein —B$^1$—B$^2$—B$^3$— is —C=N—O—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a tetramic acid compound including those selected from spirotetramat and spirodiclofen, wherein the weight ratio of A to B is 1:5 to 5:1.

In one preferred embodiment of the invention component A is a compound of formula IA, wherein —B$^1$—B$^2$—B$^3$— is —C=N—CH$_2$—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a compound as described above, wherein the weight ratio of A to B is 1:250 to 250:1.

In one preferred embodiment of the invention component A is a compound of formula IA, wherein —B$^1$—B$^2$—B$^3$— is —C=N—CH$_2$—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a compound as described above, wherein the weight ratio of A to B is 1:25 to 25:1.

In one preferred embodiment of the invention component A is a compound of formula IA, wherein —B$^1$—B$^2$—B$^3$— is —C=N—CH$_2$—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a compound as described above, wherein the weight ratio of A to B is 1:5 to 5:1.

In one preferred embodiment of the invention component A is a compound of formula IA, wherein —B$^1$—B$^2$—B$^3$— is —C=N—CH$_2$—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a tetramic acid compound including those selected from spirotetramat and spirodiclofen, or a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate wherein the weight ratio of A to B is 1:250 to 250:1.

In one preferred embodiment of the invention component A is a compound of formula IA, wherein —B$^1$—B$^2$—B$^3$— is —C=N—CH$_2$—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a tetramic acid compound including those selected from spirotetramat and spirodiclofen, or a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate wherein the weight ratio of A to B is 1:25 to 25:1.

In one preferred embodiment of the invention component A is a compound of formula IA, wherein —B$^1$—B$^2$—B$^3$— is —C=N—CH$_2$—, Y$^1$ is CH, Y$^2$ is CH, Y$^3$ is CH and R$^1$ is CF$_3$, R$^5$ is cyano, A is A2, k is 0 and X$^2$ is C—X$^6$, and component B is a tetramic acid compound including those selected from spirotetramat and spirodiclofen, or a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate wherein the weight ratio of A to B is 1:5 to 5:1.

The invention also includes the following combinations:

A mixture of a compound selected from Tables 1 to 9 and abamectin. The weight ratio of A to B may be 1:250 to 250:1, 1:25 to 25:1, in particular 1:5 to 5:1.

A mixture of a compound selected from Tables 1 to 9 and chlorpyrifos. The weight ratio of A to B may be 1:250 to 250:1, 1:25 to 25:1, in particular 1:5 to 5:1.

A mixture of a compound selected from Tables 1 to 9 and cyantraniliprole. The weight ratio of A to B may be 1:250 to 250:1, 1:25 to 25:1, in particular 1:5 to 5:1.

A mixture of a compound selected from Tables 1 to 9 and emamectin. The weight ratio of A to B may be 1:250 to 250:1, 1:25 to 25:1, in particular 1:5 to 5:1.

A mixture of a compound selected from Tables 1 to 9 and cyhalothrin. The weight ratio of A to B may be 1:250 to 250:1, 1:25 to 25:1, in particular 1:5 to 5:1.

A mixture of a compound selected from Tables 1 to 9 and lambda cyhalothrin. The weight ratio of A to B may be 1:250 to 250:1, 1:25 to 25:1, in particular 1:5 to 5:1.

A mixture of a compound selected from Tables 1 to 9 and gamma cyhalothrin. The weight ratio of A to B may be 1:250 to 250:1, 1:25 to 25:1, in particular 1:5 to 5:1.

A mixture of a compound selected from Tables 1 to 9 and pymetrozine. The weight ratio of A to B may be 1:250 to 250:1, 1:25 to 25:1, in particular 1:5 to 5:1.

A mixture of a compound selected from Tables 1 to 9 and spirotetramat. The weight ratio of A to B may be 1:250 to 250:1, 1:25 to 25:1, in particular 1:5 to 5:1.

A mixture of a compound selected from Tables 1 to 9 and thiamethoxam. The weight ratio of A to B may be 1:250 to 250:1, 1:25 to 25:1, in particular 1:5 to 5:1.

A mixture of a compound selected from Tables 1 to 9 and chlorantraniliprole. The weight ratio of A to B may be 1:250 to 250:1, 1:25 to 25:1, in particular 1:5 to 5:1.

A mixture of a compound selected from Tables 1 to 9 and profenofos. The weight ratio of A to B may be 1:250 to 250:1, 1:25 to 25:1, in particular 1:5 to 5:1.

A mixture of a compound selected from Tables 1 to 9 and acephate. The weight ratio of A to B may be 1:250 to 250:1, 1:25 to 25:1, in particular 1:5 to 5:1.

A mixture of a compound selected from Tables 1 to 9 and azinphos-methyl. The weight ratio of A to B may be 1:250 to 250:1, 1:25 to 25:1, in particular 1:5 to 5:1.

A mixture of a compound selected from Tables 1 to 9 and methamidophos. The weight ratio of A to B may be 1:250 to 250:1, 1:25 to 25:1, in particular 1:5 to 5:1.

A mixture of a compound selected from Tables 1 to 9 and spinosad. The weight ratio of A to B may be 1:250 to 250:1, 1:25 to 25:1, in particular 1:5 to 5:1.

A mixture of a compound selected from Tables 1 to 9 and spinetoram. The weight ratio of A to B may be 1:250 to 250:1, 1:25 to 25:1, in particular 1:5 to 5:1.

A mixture of a compound selected from Tables 1 to 9 and flonicamid. The weight ratio of A to B may be 1:250 to 250:1, 1:25 to 25:1, in particular 1:5 to 5:1.

A mixture of a compound selected from Tables 1 to 9 and indoxacarb. The weight ratio of A to B may be 1:250 to 250:1, 1:25 to 25:1, in particular 1:5 to 5:1.

A mixture of a compound selected from Tables 1 to 9 and spirodiclofen. The weight ratio of A to B may be 1:250 to 250:1, 1:25 to 25:1, in particular 1:5 to 5:1.

A mixture of a compound selected from Tables 1 to 9 and spiromesifen. The weight ratio of A to B may be 1:250 to 250:1, 1:25 to 25:1, in particular 1:5 to 5:1.

A mixture of a compound selected from Tables 1 to 9 and sulfoxaflor. The weight ratio of A to B may be 1:250 to 250:1, 1:25 to 25:1, in particular 1:5 to 5:1.

A mixture of a compound selected from Tables 1 to 9 and fipronil. The weight ratio of A to B may be 1:250 to 250:1, 1:25 to 25:1, in particular 1:5 to 5:1.

A mixture of a compound selected from Tables 1 to 9 and imidacloprid. The weight ratio of A to B may be 1:250 to 250:1, 1:25 to 25:1, in particular 1:5 to 5:1.

A mixture of a compound selected from Tables 1 to 9 and thiacloprid. The weight ratio of A to B may be 1:250 to 250:1, 1:25 to 25:1, in particular 1:5 to 5:1.

A mixture of a compound selected from Tables 1 to 9 and acetamiprid. The weight ratio of A to B may be 1:250 to 250:1, 1:25 to 25:1, in particular 1:5 to 5:1.

A mixture of a compound selected from Tables 1 to 9 and nitenpyram. The weight ratio of A to B may be 1:250 to 250:1, 1:25 to 25:1, in particular 1:5 to 5:1.

A mixture of a compound selected from Tables 1 to 9 and dinotefuran. The weight ratio of A to B may be 1:250 to 250:1, 1:25 to 25:1, in particular 1:5 to 5:1.

A mixture of a compound selected from Tables 1 to 9 and clothianidin. The weight ratio of A to B may be 1:250 to 250:1, 1:25 to 25:1, in particular 1:5 to 5:1.

A mixture of a compound selected from Tables 1 to 9 and nithiazine. The weight ratio of A to B may be 1:250 to 250:1, 1:25 to 25:1, in particular 1:5 to 5:1.

A mixture of a compound selected from Tables 1 to 9 and pyriproxyfen. The weight ratio of A to B may be 1:250 to 250:1, 1:25 to 25:1, in particular 1:5 to 5:1.

A mixture of a compound selected from Tables 1 to 9 and buprofezin. The weight ratio of A to B may be 1:250 to 250:1, 1:25 to 25:1, in particular 1:5 to 5:1.

A mixture of a compound selected from Tables 1 to 9 and pyrifluqinazon. The weight ratio of A to B may be 1:250 to 250:1, 1:25 to 25:1, in particular 1:5 to 5:1.

A mixture of a compound selected from Tables 1 to 9 thiamethoxam and cyantraniliprole. The weight ratio of A to B may be 1:250 to 250:1, 1:25 to 25:1, in particular 1:5 to 5:1.

A mixture of a compound selected from Tables 1 to 9 thiamethoxam and chlorantraniliprole. The weight ratio of A to B may be 1:250 to 250:1, 1:25 to 25:1, in particular 1:5 to 5:1.

A mixture of a compound selected from Tables 1 to 9 and sulfoxaflor. The weight ratio of A to B may be 1:250 to 250:1, 1:25 to 25:1, in particular 1:5 to 5:1.

A mixture of a compound selected from Tables 1 to 9 and Lufeneron. The weight ratio of A to B may be 1:250 to 250:1, 1:25 to 25:1, in particular 1:5 to 5:1.

A mixture of a compound selected from Tables 1 to 9 Diafenthiuron. The weight ratio of A to B may be 1:250 to 250:1, 1:25 to 25:1, in particular 1:5 to 5:1.

A mixture of a compound selected from Tables 1 to 9 and Flubendiamide. The weight ratio of A to B may be 1:250 to 250:1, 1:25 to 25:1, in particular 1:5 to 5:1.

A mixture of a compound selected from Tables 1 to 9 and Tefluthrin. The weight ratio of A to B may be 1:250 to 250:1, 1:25 to 25:1, in particular 1:5 to 5:1.

A mixture of a compound selected from Tables 1 to 9 and Fipronil. The weight ratio of A to B may be 1:250 to 250:1, 1:25 to 25:1, in particular 1:5 to 5:1.

A mixture of a compound selected from Tables 1 to 9 and Ethiprole. The weight ratio of A to B may be 1:250 to 250:1, 1:25 to 25:1, in particular 1:5 to 5:1.

A mixture of a compound selected from Tables 1 to 9 and Flupyradifurone. The weight ratio of A to B may be 1:250 to 250:1, 1:25 to 25:1, in particular 1:5 to 5:1.

A mixture of a compound selected from Tables 1 to 9 and Iprodione. The weight ratio of A to B may be 1:250 to 250:1, 1:25 to 25:1, in particular 1:5 to 5:1.

A mixture of a compound selected from Tables 1 to 9 and Thiodicarb. The weight ratio of A to B may be 1:250 to 250:1, 1:25 to 25:1, in particular 1:5 to 5:1.

A mixture of a compound selected from Tables 1 to 9 and Deltamethrin. The weight ratio of A to B may be 1:250 to 250:1, 1:25 to 25:1, in particular 1:5 to 5:1.

A mixture of a compound selected from Tables 1 to 9 and beta-Cyfluthrin. The weight ratio of A to B may be 1:250 to 250:1, 1:25 to 25:1, in particular 1:5 to 5:1.

A mixture of a compound selected from Tables 1 to 9 and Aldicarb. The weight ratio of A to B may be 1:250 to 250:1, 1:25 to 25:1, in particular 1:5 to 5:1.

A mixture of a compound selected from Tables 1 to 9 and -4-[[(6-Chloropyridin-3-yl)methyl](2,2-difluoroethyl)amino]furan-2(5H)-one. The weight ratio of A to B may be 1:250 to 250:1, 1:25 to 25:1, in particular 1:5 to 5:1.

A mixture of a compound selected from Tables 1 to 9 and imidacloprid and Beta-cyfluthrin. The weight ratio of A to B may be 1:250 to 250:1, 1:25 to 25:1, in particular 1:5 to 5:1.

The invention also includes the following combinations:

A mixture of a compound selected from Table 1 and abamectin. The weight ratio of A to B may be 1:250 to 250:1, 1:25 to 25:1, in particular 1:5 to 5:1.

A mixture of a compound selected from Table 1 and chlorpyrifos. The weight ratio of A to B may be 1:250 to 250:1, 1:25 to 25:1, in particular 1:5 to 5:1.

A mixture of a compound selected from Table 1 and cyantraniliprole. The weight ratio of A to B may be 1:250 to 250:1, 1:25 to 25:1, in particular 1:5 to 5:1.

A mixture of a compound selected from Table 1 and emamectin. The weight ratio of A to B may be 1:250 to 250:1, 1:25 to 25:1, in particular 1:5 to 5:1.

A mixture of a compound selected from Table 1 and cyhalothrin. The weight ratio of A to B may be 1:250 to 250:1, 1:25 to 25:1, in particular 1:5 to 5:1.

A mixture of a compound selected from Table 1 and lambda cyhalothrin. The weight ratio of A to B may be 1:250 to 250:1, 1:25 to 25:1, in particular 1:5 to 5:1.

A mixture of a compound selected from Table 1 and gamma cyhalothrin. The weight ratio of A to B may be 1:250 to 250:1, 1:25 to 25:1, in particular 1:5 to 5:1.

A mixture of a compound selected from Table 1 and pymetrozine. The weight ratio of A to B may be 1:250 to 250:1, 1:25 to 25:1, in particular 1:5 to 5:1.

A mixture of a compound selected from Table 1 and spirotetramat. The weight ratio of A to B may be 1:250 to 250:1, 1:25 to 25:1, in particular 1:5 to 5:1.

A mixture of a compound selected from Table 1 and thiamethoxam. The weight ratio of A to B may be 1:250 to 250:1, 1:25 to 25:1, in particular 1:5 to 5:1.

A mixture of a compound selected from Table 1 and chlorantraniliprole. The weight ratio of A to B may be 1:250 to 250:1, 1:25 to 25:1, in particular 1:5 to 5:1.

A mixture of a compound selected from Table 1 and profenofos. The weight ratio of A to B may be 1:250 to 250:1, 1:25 to 25:1, in particular 1:5 to 5:1.

A mixture of a compound selected from Table 1 and acephate. The weight ratio of A to B may be 1:250 to 250:1, 1:25 to 25:1, in particular 1:5 to 5:1.

A mixture of a compound selected from Table 1 and azinphos-methyl. The weight ratio of A to B may be 1:250 to 250:1, 1:25 to 25:1, in particular 1:5 to 5:1.

A mixture of a compound selected from Table 1 and methamidophos. The weight ratio of A to B may be 1:250 to 250:1, 1:25 to 25:1, in particular 1:5 to 5:1.

A mixture of a compound selected from Table 1 and spinosad. The weight ratio of A to B may be 1:250 to 250:1, 1:25 to 25:1, in particular 1:5 to 5:1.

A mixture of a compound selected from Table 1 and spinetoram. The weight ratio of A to B may be 1:250 to 250:1, 1:25 to 25:1, in particular 1:5 to 5:1.

A mixture of a compound selected from Table 1 and flonicamid. The weight ratio of A to B may be 1:250 to 250:1, 1:25 to 25:1, in particular 1:5 to 5:1.

A mixture of a compound selected from Table 1 and indoxacarb. The weight ratio of A to B may be 1:250 to 250:1, 1:25 to 25:1, in particular 1:5 to 5:1.

A mixture of a compound selected from Table 1 and spirodiclofen. The weight ratio of A to B may be 1:250 to 250:1, 1:25 to 25:1, in particular 1:5 to 5:1.

A mixture of a compound selected from Table 1 and spiromesifen. The weight ratio of A to B may be 1:250 to 250:1, 1:25 to 25:1, in particular 1:5 to 5:1.

A mixture of a compound selected from Table 1 and sulfoxaflor. The weight ratio of A to B may be 1:250 to 250:1, 1:25 to 25:1, in particular 1:5 to 5:1.

A mixture of a compound selected from Table 1 and fipronil. The weight ratio of A to B may be 1:250 to 250:1, 1:25 to 25:1, in particular 1:5 to 5:1.

A mixture of a compound selected from Table 1 and imidacloprid. The weight ratio of A to B may be 1:250 to 250:1, 1:25 to 25:1, in particular 1:5 to 5:1.

A mixture of a compound selected from Table 1 and thiacloprid. The weight ratio of A to B may be 1:250 to 250:1, 1:25 to 25:1, in particular 1:5 to 5:1.

A mixture of a compound selected from Table 1 and acetamiprid. The weight ratio of A to B may be 1:250 to 250:1, 1:25 to 25:1, in particular 1:5 to 5:1.

A mixture of a compound selected from Table 1 and nitenpyram. The weight ratio of A to B may be 1:250 to 250:1, 1:25 to 25:1, in particular 1:5 to 5:1.

A mixture of a compound selected from Table 1 and dinotefuran. The weight ratio of A to B may be 1:250 to 250:1, 1:25 to 25:1, in particular 1:5 to 5:1.

A mixture of a compound selected from Table 1 and clothianidin. The weight ratio of A to B may be 1:250 to 250:1, 1:25 to 25:1, in particular 1:5 to 5:1.

A mixture of a compound selected from Table 1 and nithiazine. The weight ratio of A to B may be 1:250 to 250:1, 1:25 to 25:1, in particular 1:5 to 5:1.

A mixture of a compound selected from Table 1 and pyriproxyfen. The weight ratio of A to B may be 1:250 to 250:1, 1:25 to 25:1, in particular 1:5 to 5:1.

A mixture of a compound selected from Table 1 and buprofezin. The weight ratio of A to B may be 1:250 to 250:1, 1:25 to 25:1, in particular 1:5 to 5:1.

A mixture of a compound selected from Table 1 and pyrifluqinazon. The weight ratio of A to B may be 1:250 to 250:1, 1:25 to 25:1, in particular 1:5 to 5:1.

A mixture of a compound selected from Table 1 thiamethoxam and cyantraniliprole. The weight ratio of A to B may be 1:250 to 250:1, 1:25 to 25:1, in particular 1:5 to 5:1.

A mixture of a compound selected from Table 1 thiamethoxam and chlorantraniliprole. The weight ratio of A to B may be 1:250 to 250:1, 1:25 to 25:1, in particular 1:5 to 5:1.

A mixture of a compound selected from Table 1 and sulfoxaflor. The weight ratio of A to B may be 1:250 to 250:1, 1:25 to 25:1, in particular 1:5 to 5:1.

A mixture of a compound selected from Table 1 and Lufeneron. The weight ratio of A to B may be 1:250 to 250:1, 1:25 to 25:1, in particular 1:5 to 5:1.

A mixture of a compound selected from Table 1 Diafenthiuron. The weight ratio of A to B may be 1:250 to 250:1, 1:25 to 25:1, in particular 1:5 to 5:1.

A mixture of a compound selected from Table 1 and Flubendiamide. The weight ratio of A to B may be 1:250 to 250:1, 1:25 to 25:1, in particular 1:5 to 5:1.

A mixture of a compound selected from Table 1 and Tefluthrin. The weight ratio of A to B may be 1:250 to 250:1, 1:25 to 25:1, in particular 1:5 to 5:1.

A mixture of a compound selected from Table 1 and Fipronil. The weight ratio of A to B may be 1:250 to 250:1, 1:25 to 25:1, in particular 1:5 to 5:1.

A mixture of a compound selected from Table 1 and Ethiprole. The weight ratio of A to B may be 1:250 to 250:1, 1:25 to 25:1, in particular 1:5 to 5:1.

A mixture of a compound selected from Table 1 and Flupyradifurone. The weight ratio of A to B may be 1:250 to 250:1, 1:25 to 25:1, in particular 1:5 to 5:1.

A mixture of a compound selected from Table 1 and Iprodione. The weight ratio of A to B may be 1:250 to 250:1, 1:25 to 25:1, in particular 1:5 to 5:1.

A mixture of a compound selected from Table 1 and Thiodicarb. The weight ratio of A to B may be 1:250 to 250:1, 1:25 to 25:1, in particular 1:5 to 5:1.

A mixture of a compound selected from Table 1 and Deltamethrin. The weight ratio of A to B may be 1:250 to 250:1, 1:25 to 25:1, in particular 1:5 to 5:1.

A mixture of a compound selected from Table 1 and beta-Cyfluthrin. The weight ratio of A to B may be 1:250 to 250:1, 1:25 to 25:1, in particular 1:5 to 5:1.

A mixture of a compound selected from Table 1 and Aldicarb. The weight ratio of A to B may be 1:250 to 250:1, 1:25 to 25:1, in particular 1:5 to 5:1.

A mixture of a compound selected from Table 1 and -4-[[(6-Chloropyridin-3-yl)methyl](2,2-difluoroethyl) amino]furan-2(5H)-one. The weight ratio of A to B may be 1:250 to 250:1, 1:25 to 25:1, in particular 1:5 to 5:1.

A mixture of a compound selected from Table 1 and imidacloprid and Beta-cyfluthrin. The weight ratio of A to B may be 1:250 to 250:1, 1:25 to 25:1, in particular 1:5 to 5:1.

The invention also includes the following combinations:

A mixture of a compound selected from Table 2 and abamectin. The weight ratio of A to B may be 1:250 to 250:1, 1:25 to 25:1, in particular 1:5 to 5:1.

A mixture of a compound selected from Table 2 and chlorpyrifos. The weight ratio of A to B may be 1:250 to 250:1, 1:25 to 25:1, in particular 1:5 to 5:1.

A mixture of a compound selected from Table 2 and cyantraniliprole. The weight ratio of A to B may be 1:250 to 250:1, 1:25 to 25:1, in particular 1:5 to 5:1.

A mixture of a compound selected from Table 2 and emamectin. The weight ratio of A to B may be 1:250 to 250:1, 1:25 to 25:1, in particular 1:5 to 5:1.

A mixture of a compound selected from Table 2 and cyhalothrin. The weight ratio of A to B may be 1:250 to 250:1, 1:25 to 25:1, in particular 1:5 to 5:1.

A mixture of a compound selected from Table 2 and lambda cyhalothrin. The weight ratio of A to B may be 1:250 to 250:1, 1:25 to 25:1, in particular 1:5 to 5:1.

A mixture of a compound selected from Table 2 and gamma cyhalothrin. The weight ratio of A to B may be 1:250 to 250:1, 1:25 to 25:1, in particular 1:5 to 5:1.

A mixture of a compound selected from Table 2 and pymetrozine. The weight ratio of A to B may be 1:250 to 250:1, 1:25 to 25:1, in particular 1:5 to 5:1.

A mixture of a compound selected from Table 2 and spirotetramat. The weight ratio of A to B may be 1:250 to 250:1, 1:25 to 25:1, in particular 1:5 to 5:1.

A mixture of a compound selected from Table 2 and thiamethoxam. The weight ratio of A to B may be 1:250 to 250:1, 1:25 to 25:1, in particular 1:5 to 5:1.

A mixture of a compound selected from Table 2 and chlorantraniliprole. The weight ratio of A to B may be 1:250 to 250:1, 1:25 to 25:1, in particular 1:5 to 5:1.

A mixture of a compound selected from Table 2 and profenofos. The weight ratio of A to B may be 1:250 to 250:1, 1:25 to 25:1, in particular 1:5 to 5:1.

A mixture of a compound selected from Table 2 and acephate. The weight ratio of A to B may be 1:250 to 250:1, 1:25 to 25:1, in particular 1:5 to 5:1.

A mixture of a compound selected from Table 2 and azinphos-methyl. The weight ratio of A to B may be 1:250 to 250:1, 1:25 to 25:1, in particular 1:5 to 5:1.

A mixture of a compound selected from Table 2 and methamidophos. The weight ratio of A to B may be 1:250 to 250:1, 1:25 to 25:1, in particular 1:5 to 5:1.

A mixture of a compound selected from Table 2 and spinosad. The weight ratio of A to B may be 1:250 to 250:1, 1:25 to 25:1, in particular 1:5 to 5:1.

A mixture of a compound selected from Table 2 and spinetoram. The weight ratio of A to B may be 1:250 to 250:1, 1:25 to 25:1, in particular 1:5 to 5:1.

A mixture of a compound selected from Table 2 and flonicamid. The weight ratio of A to B may be 1:250 to 250:1, 1:25 to 25:1, in particular 1:5 to 5:1.

A mixture of a compound selected from Table 2 and indoxacarb. The weight ratio of A to B may be 1:250 to 250:1, 1:25 to 25:1, in particular 1:5 to 5:1.

A mixture of a compound selected from Table 2 and spirodiclofen. The weight ratio of A to B may be 1:250 to 250:1, 1:25 to 25:1, in particular 1:5 to 5:1.

A mixture of a compound selected from Table 2 and spiromesifen. The weight ratio of A to B may be 1:250 to 250:1, 1:25 to 25:1, in particular 1:5 to 5:1.

A mixture of a compound selected from Table 2 and sulfoxaflor. The weight ratio of A to B may be 1:250 to 250:1, 1:25 to 25:1, in particular 1:5 to 5:1.

A mixture of a compound selected from Table 2 and fipronil. The weight ratio of A to B may be 1:250 to 250:1, 1:25 to 25:1, in particular 1:5 to 5:1.

A mixture of a compound selected from Table 2 and imidacloprid. The weight ratio of A to B may be 1:250 to 250:1, 1:25 to 25:1, in particular 1:5 to 5:1.

A mixture of a compound selected from Table 2 and thiacloprid. The weight ratio of A to B may be 1:250 to 250:1, 1:25 to 25:1, in particular 1:5 to 5:1.

A mixture of a compound selected from Table 2 and acetamiprid. The weight ratio of A to B may be 1:250 to 250:1, 1:25 to 25:1, in particular 1:5 to 5:1.

A mixture of a compound selected from Table 2 and nitenpyram. The weight ratio of A to B may be 1:250 to 250:1, 1:25 to 25:1, in particular 1:5 to 5:1.

A mixture of a compound selected from Table 2 and dinotefuran. The weight ratio of A to B may be 1:250 to 250:1, 1:25 to 25:1, in particular 1:5 to 5:1.

A mixture of a compound selected from Table 2 and clothianidin. The weight ratio of A to B may be 1:250 to 250:1, 1:25 to 25:1, in particular 1:5 to 5:1.

A mixture of a compound selected from Table 2 and nithiazine. The weight ratio of A to B may be 1:250 to 250:1, 1:25 to 25:1, in particular 1:5 to 5:1.

A mixture of a compound selected from Table 2 and pyriproxyfen. The weight ratio of A to B may be 1:250 to 250:1, 1:25 to 25:1, in particular 1:5 to 5:1.

A mixture of a compound selected from Table 2 and buprofezin. The weight ratio of A to B may be 1:250 to 250:1, 1:25 to 25:1, in particular 1:5 to 5:1.

A mixture of a compound selected from Table 2 and pyrifluqinazon. The weight ratio of A to B may be 1:250 to 250:1, 1:25 to 25:1, in particular 1:5 to 5:1.

A mixture of a compound selected from Table 2 thiamethoxam and cyantraniliprole. The weight ratio of A to B may be 1:250 to 250:1, 1:25 to 25:1, in particular 1:5 to 5:1.

A mixture of a compound selected from Table 2 thiamethoxam and chlorantraniliprole. The weight ratio of A to B may be 1:250 to 250:1, 1:25 to 25:1, in particular 1:5 to 5:1.

A mixture of a compound selected from Table 2 and sulfoxaflor. The weight ratio of A to B may be 1:250 to 250:1, 1:25 to 25:1, in particular 1:5 to 5:1.

A mixture of a compound selected from Table 2 and Lufeneron. The weight ratio of A to B may be 1:250 to 250:1, 1:25 to 25:1, in particular 1:5 to 5:1.

A mixture of a compound selected from Table 2 Diafenthiuron. The weight ratio of A to B may be 1:250 to 250:1, 1:25 to 25:1, in particular 1:5 to 5:1.

A mixture of a compound selected from Table 2 and Flubendiamide. The weight ratio of A to B may be 1:250 to 250:1, 1:25 to 25:1, in particular 1:5 to 5:1.

A mixture of a compound selected from Table 2 and Tefluthrin. The weight ratio of A to B may be 1:250 to 250:1, 1:25 to 25:1, in particular 1:5 to 5:1.

A mixture of a compound selected from Table 2 and Fipronil. The weight ratio of A to B may be 1:250 to 250:1, 1:25 to 25:1, in particular 1:5 to 5:1.

A mixture of a compound selected from Table 2 and Ethiprole. The weight ratio of A to B may be 1:250 to 250:1, 1:25 to 25:1, in particular 1:5 to 5:1.

A mixture of a compound selected from Table 2 and Flupyradifurone. The weight ratio of A to B may be 1:250 to 250:1, 1:25 to 25:1, in particular 1:5 to 5:1.

A mixture of a compound selected from Table 2 and Iprodione. The weight ratio of A to B may be 1:250 to 250:1, 1:25 to 25:1, in particular 1:5 to 5:1.

A mixture of a compound selected from Table 2 and Thiodicarb. The weight ratio of A to B may be 1:250 to 250:1, 1:25 to 25:1, in particular 1:5 to 5:1.

A mixture of a compound selected from Table 2 and Deltamethrin. The weight ratio of A to B may be 1:250 to 250:1, 1:25 to 25:1, in particular 1:5 to 5:1.

A mixture of a compound selected from Table 2 and beta-Cyfluthrin. The weight ratio of A to B may be 1:250 to 250:1, 1:25 to 25:1, in particular 1:5 to 5:1.

A mixture of a compound selected from Table 2 and Aldicarb. The weight ratio of A to B may be 1:250 to 250:1, 1:25 to 25:1, in particular 1:5 to 5:1.

A mixture of a compound selected from Table 2 and -4-[[(6-Chloropyridin-3-yl)methyl](2,2-difluoroethyl)amino]furan-2(5H)-one. The weight ratio of A to B may be 1:250 to 250:1, 1:25 to 25:1, in particular 1:5 to 5:1.

A mixture of a compound selected from Table 2 and imidacloprid and Beta-cyfluthrin. The weight ratio of A to B may be 1:250 to 250:1, 1:25 to 25:1, in particular 1:5 to 5:1.

The present invention also relates to a method of controlling insects, acarines, nematodes or molluscs which comprises applying to a pest, to a locus of a pest, or to a plant susceptible to attack by a pest a combination of components A and B; seeds comprising a mixture of components A and B; and a method comprising coating a seed with a mixture of components A and B.

Components A and B may be provided and/or used in amounts such that they are capable of synergistic pest control. For example, the present invention includes pesticidal mixtures comprising a component A and a component B in a synergistically effective amount; agricultural compositions comprising a mixture of component A and B in a synergistically effective amount; the use of a mixture of component A and B in a synergistically effective amount for combating animal pests; a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a mixture of component A and B in a synergistically effective amount; a method for protecting crops from attack or infestation by animal pests which comprises contacting a crop with a mixture of component A and B in a synergistically effective amount; a method for the protection of seeds from soil insects and of the seedlings' roots and shoots from soil and foliar insects comprising contacting the seeds before sowing and/or after pre-germination with a mixture of component A and B in a synergistically effective amount; seeds comprising, e.g. coated with, a mixture of component A and B in a synergistically effective amount; a method comprising coating a seed with a mixture of component A and B in a synergistically effective amount; a method of controlling insects, acarines, nematodes or molluscs which comprises applying to a pest, to a locus of a pest, or to a plant susceptible to attack by a pest a combination of components A and B in a synergistically effective amount. Mixtures of A and B will normally be applied in an insecticidally, acaricidally, nematicidally or molluscicidally effective amount. In application components A and B may be applied simultaneously or separately.

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation. It may be noted that compound of formula I may also be used for controlling insect, acaricide, mollusc and/or nematode pests on turf in the absence of mixing partners.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Compounds of formula I and mixtures of the invention may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive "synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected. Such synergistic effects with the transgenic crop can be obtained when applied for control of soil pests (e.g. seed care or in-furrow treatments) as well as after emergence, in particular for corn and soybean.

Use of the compounds of formula I and the mixtures of the invention can also be applied as a seed care treatment with transgenic crops in resistance management strategies for the trait (particularly inseciticidal traits), e.g. including in corn and soybean.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A.105, Cry2Ab2, Cry1F, Cry34/35, Cry3Bb); Herculex® I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT® (cotton cultivars producing a Vip3Aa). Soybean Cyst Nematode resistance soybean (SCN®—Syngenta) and soybean with Aphid resistant trait (AMT®) are also of interest.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4D (e.g. Enlist®) (e.g. WO 2011066384), glyphosate (e.g.

Roundup Ready®, Roundup Ready 2 Yield®), sulfonylurea (e.g. STS®), glufosinate (e.g. Liberty Link®, Ignite®), Dicamba (Monsanto), HPPD tolerance (e.g. isoxaflutole herbicide) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®), dicamba and glyphosate tolerance (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®—Monsanto), MON1445 (Roundup ready Cotton®—Monsanto), MON531×MON1445 (Bollgard I+RR®—Monsanto), MON15985 (Genuity Bollgard II Cotton®—Monsanto), MON88913 (Genuity RR FLEX Cotton®—Monsanto), MON15985×MON1445 (Genuity Bollgard II+RR FELX Cotton®—Monsanto), MON15983×MON88913 (Genuity Bollgard II+RR FLEX Cotton®—Monsanto), MON15985 (FibreMax Bollgard II Cotton®—Monsanto), LL25 (FibreMax LL Cotton®—BCS Stoneville), GHB614 (FibreMax GlyTol Cotton®—BCS Stoneville), LL25×MON15985 (FibreMax LL Bollgard II Cotton®—BCS Stoneville/Monsanto), GHB614×LL25 (FibreMax LL GlyTol Cotton®—BCS Stoneville), GHB614×LL25×MON15985 (FibreMax RR GlyTol Bollgard II Cotton®—BCS Stoneville), MON88913×MON15985 (FibreMax LL GlyTol Bollgard II Cotton®—Monsanto), MON88913 (FibreMax RR Flex Cotton®—Monsanto), GHB119+T304-40 (Twinlink®—BCS Stoneville), GHB119+T304-40×LL25×GHB614 (Twinlink LL GT®—BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX—® Dow/Monsanto), 3006-210-23×281-24-236×MON1445 ((PhytoGen Widestrike Insect Protection+RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102×COT67B×MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701×MON89788 (Genuity Roundup ready 2 Yield Soybeans®—Monsanto), MON89788 (Roundup Ready2Yield®, RR2Y®—Monsanto), MON87708 (Monsanto), 40-3-2 (Roundup Ready®, RR1®—Monsanto), MON87701 (Monsanto), DAS-68416 (Enlist Weed Control System®—Dow), DP356043 (Optimum GAT®—Pioneer), A5547-127 (LibertyLink Soybean®—Bayercropscience), A2704-12 (Bayercropscience), GU262 (Bayercropscience), W62 W98 (Bayercropscience), CRV127 (Cultivance®—BASF/EMBRAPA) SYHT0H2 (WO2012/082548).

Examples of Maize transgenic events include T25 (LibertyLink®, LL®—Bayerscropscience), DHT-1 (Dow), TC1507 (Herculex I®—Dow), DAS59122-7 (Herculex RW®—Dow), TC1507+DAS59122-7—Herculex Xtra®—Dow), TC1507×DAS-59122-7×NK603 (Herculex Xtra+RR®—Dow), TC1507×DAS-59122-×MON88017×MON89034 (Genuity Smartstax Corn®, Genuity Smartstax RIB Complete®—Monsanto/Dow), MON89034×NK603 (Genuity VT double PRO®—Monsanto), MON89034+MON88017 (Genuity VT Triple PRO®—Monsanto), NK603 (Roundup Ready 2®, RR2®—Monsanto), MON810 (YieldGard BT®, Yieldgard Cornborer®—Monsanto), MON810×NK603 (YieldGard cornborer RR Corn 2®—Monasnto), MON810×MON863 (YieldGard Plus®—Monsanto), MON863×MON810×NK603 (YieldGard Plus+RR Corn2®/YieldGard RR Maize®—Monsanto), MON863×NK603 (YieldGard Rotworm+RR Corn 2®—Monsanto), MON863 (YieldBard RW®—Monsanto), MON89034 (YieldGard RW®—Monsanto), MON88017 (YieldGard VT RW®—Monsanto), MON810+MON88017 (YieldGard VT Triple®—Monsanto), MON88017+MON89034 (YieldGard VT Triple Pro®—Monsanto), Bt11+MIR604+GA21 (Agrisure 3000®—Syngenta), Bt11+TC1507+MIR604+5307+GA21 (Syngenta), Bt11+TC1507+MIR604+DAS59122+GA21 (Agrisure 3122®—Syngenta), BT11 (Agrisure CB®—Syngenta), GA21—(Agrisure GT®—Syngenta), MIR604 (Agrisure RW®—Syngenta), Bt11+MIR162 (Agrisure TL VIP®—Syngenta), BT11+MIR162+GA21 (Agrisure Viptra 3110®—Syngenta), BT11+MIR162+MIR604 (Agrisure™ 3100®—Syngenta), Event3272+BT11+MIR604+GA21 (Syngenta), BT11+MIR1692+MIR604+GA21 (Agrisure Viptera 3111®—Syngenta), BT11+MIR 162+TC1507+GA21 (Agrisure Viptera 3220®—Syngenta), BT11+MIR162+TC1507+MIR604+5307+GA21 (Agrisure Viptera 3222®—Syngenta), MIR162 (Syngenta), BT11+GA21+MIR162+MIR604+5307 (Syngenta), 5307 (Syngenta).

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds. Insecticides that are of particular interest for treating seeds include thiamethoxam, imidacloprid and clothianidin. Accordingly, in one embodiment component B is selected from thiamethoxam, imidacloprid and clothianidin.

Methods for applying or treating active ingredients on to plant propagation material, especially seeds, are known in the art, and include dressing, coating, pelleting and soaking application methods of the propagation material. Conventional treating techniques and machines can be used, such as fluidized beds, roller mills, rotostatic seed treaters, drum coaters, and spouted beds.

Methods of applying to the soil can be via any suitable method, which ensures that the combination penetrates the soil, for example, nursery tray application, in furrow application, soil drenching, soil injection, drip irrigation, application through sprinklers or central pivot, incorporation into soil (broad cast or in band) are such methods. Alternatively or in addition one or more materials may be applied on a suitable substrate, for example a seed which is not intended for germination, and "sowing" the treated substrate with the plant propagation material.

Even distribution of ingredients and good adherence is particularly desired for seed treatment. Treatment could vary from a thin film or dressing of the formulation, for example, a mixture of active ingredients, on a plant propagation material, such as a seed, where the original size and/or shape are recognizable to an intermediary state to a thicker film such as pelleting with many layers of different materials (such as carriers, for example, clays; different formulations, such as of other active ingredients; polymers; and colourants) where the original shape and/or size of the seed is no longer recognisable.

Application onto plant propagation material can include controlled release coatings, wherein the ingredients of the combinations are incorporated into materials that release the ingredients over time. Examples of controlled release technologies are generally known in the art and include polymer films and waxes, wherein the ingredients may be incorporated into the controlled release material or applied between layers of materials, or both.

A further aspect of the instant invention is a method of protecting natural substances of plant and/or animal origin, which have been taken from the natural life cycle, and/or their processed forms against attack of pests, which comprises applying to said natural substances of plant and/or animal origin or their processed forms a combination of components A and B in a synergistically effective amount. Such applications include use of the mixtures of the invention as a treatment, for example a fumigant, for stored grain to protect against attack of invertabrate pests and or fungi. It may be noted that compounds of formula I may be used alone as a treatment for stored grain to protect against attack of invertabrate pests.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like.

A preferred embodiment is a method of protecting natural substances of plant origin, which have been taken from the natural life cycle, and/or their processed forms against attack of pests, which comprises applying to said natural substances of plant and/or animal origin or their processed forms a combination of components A and B in a synergistically effective amount.

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a combination of components A and B in a synergistically effective amount.

The mixtures of the invention can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounsd of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the mixtures of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount applied, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by mixtures of the invention include: *coleopterans*, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus, Aulacophora femoralis; lepidopterans*, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella; hemipterans*, for example, *Nephotettix cincticeps, Nilaparvata lugens, Pseudococcus comstocki, Unaspis yanonensis, Myzus per-* sicas, Aphis pomi, Aphis gossypii, Rhopalosiphum pseudobrassicas, Stephanitis nashi, Nezara spp., Trialeurodes vaporariorm, Psylla spp.; thysanopterans, for example, Thrips palmi, Franklinella occidental; orthopterans, for example, Blatella germanica, Periplaneta americana, Gryllotalpa Africana, Locusta migratoria migratoriodes; isopterans, for example, Reticulitermes speratus, Coptotermes formosanus; dipterans, for example, Musca domestica, Aedes aegypti, Hylemia platura, Culex pipiens, Anopheles sinensis, Culex tritaeniorhynchus, Liriomyza trifolii; acari, for example, Tetranychus cinnabarinus, Tetranychus urticae, Panonychus citri, Aculops pelekassi, Tarsonemus spp.; nematodes, for example, Meloidogyne incognita, Bursaphelenchus lignicolus Mamiya et Kiyohara, Aphelenchoides besseyi, Heterodera glycines, Pratylenchus spp.

Examples of further pest species which may be controlled by mixtures of the invention include: from the order of the Anoplura (Phthiraptera), for example, Damalinia spp., Haematopinus spp., Linognathus spp., Pediculus spp., Trichodectes spp.; from the class of the Arachnida, for example, Acarus siro, Aceria sheldoni, Aculops spp., Aculus spp., Amblyomma spp., Argas spp., Boophilus spp., Brevipalpus spp., Bryobia praetiosa, Chorioptes spp., Dermanyssus gallinae, Eotetranychus spp., Epitrimerus pyri, Eutetranychus spp., Eriophyes spp., Hemitarsonemus spp., Hyalomma spp., Ixodes spp., Latrodectus mactans, Metatetranychus spp., Oligonychus spp., Ornithodoros spp., Panonychus spp., Phyllocoptruta oleivora, Polyphagotarsonemus latus, Psoroptes spp., Rhipicephalus spp., Rhizoglyphus spp., Sarcoptes spp., Scorpio maurus, Stenotarsonemus spp., Tarsonemus spp., Tetranychus spp., Vasates lycopersici; from the class of the Bivalva, for example, Dreissena spp.; from the order of the Chilopoda, for example, Geophilus spp., Scutigera spp.; from the order of the Coleoptera, for example, Acanthoscehdes obtectus, Adoretus spp., Agelastica alni, Agriotes spp., Amphimallon solstitialis, Anobium punctatum, Anoplophora spp., Anthonomus spp., Anthrenus spp., Apogonia spp., Atomaria spp., Attagenus spp., Bruchidius obtectus, Bruchus spp., Ceuthorhynchus spp., Cleonus mendicus, Conoderus spp., Cosmopolites spp., Costelytra zealandica, Curculio spp., Cryptorhynchus lapathi, Dermestes spp., Diabrotica spp., Epilachna spp., Faustinus cubae, Gibbium psylloides, Heteronychus arator, Hylamorpha elegans, Hylotrupes bajulus, Hypera postica, Hypothenemus spp., Lachnosterna consanguinea, Leptinotarsa decemlineata, Lissorhoptrus oryzophilus, Lixus spp., Lyctus spp., Meligethes aeneus, Melolontha melolontha, Migdolus spp., Monochamus spp., Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga spp., Popillia japonica, Premnotrypes spp., Psylliodes chrysocephala, Ptinus spp., Rhizobius ventralis, Rhizopertha dominica, Sitophilus spp., Sphenophorus spp., Sternechus spp., Symphyletes spp., Tenebrio molitor, Tribolium spp., Trogoderma spp., Tychius spp., Xylotrechus spp., Zabrus spp.; from the order of the Collembola, for example, Onychiurus armatus; from the order of the Dermaptera, for example, Forficula auricularia; from the order of the Diplopoda, for example, Blaniulus guttulatus; from the order of the Diptera, for example, Aedes spp., Anopheles spp., Bibio hortulanus, Calliphora erythrocephala, Ceratitis capitata, Chrysomyia spp., Cochliomyia spp., Cordylobia anthropophaga, Culex spp., Cuterebra spp., Dacus oleae, Dermatobia hominis, Drosophila spp., Fannia spp., Gastrophilus spp., Hylemyia spp., Hyppobosca spp., Hypoderma spp., Liriomyza spp., Lucilia spp., Musca spp., Nezara spp., Oestrus spp., Oscinella frit, Pegomyia hyoscyami, Phorbia spp., Stomoxys spp., Tabanus spp., Tannia spp., Tipula paludosa, Wohlfahrtia spp.; from the class of the Gastropoda, for example, Arion spp., Biomphalaria spp., Bulinus spp., Deroceras spp., Galba spp., Lymnaea spp., Oncomelania spp., Succinea spp.; from the class of the helminths, for example, Ancylostoma duodenale, Ancylostoma ceylanicum, Acylostoma braziliensis, Ancylostoma spp., Ascaris lubricoides, Ascaris spp., Brugia malayi, Brugia timori, Bunostomum spp., Chabertia spp., Clonorchis spp., Cooperia spp., Dicrocoelium spp, Dictyocaulus filaria, Diphyllobothrium latum, Dracunculus medinensis, Echinococcus granulosus, Echinococcus multilocularis, Enterobius vermicularis, Faciola spp., Haemonchus spp., Heterakis spp., Hymenolepis nana, Hyostrongulus spp., Loa Loa, Nematodirus spp., Oesophagostomum spp., Opisthorchis spp., Onchocerca volvulus, Ostertagia spp., Paragonimus spp., Schistosomen spp., Strongyloides fuelleborni, Strongyloides stercoralis, Stronyloides spp., Taenia saginata, Taenia solium, Trichinella spiralis, Trichinella nativa, Trichinella britovi, Trichinella nelsoni, Trichinella pseudopsiralis, Trichostrongulus spp., Trichuris trichiura, Wuchereria bancrofti; ft may be furthermore possible to control protozoa, such as Eimeria; from the order of the Heteroptera, for example, Anasa tristis, Antestiopsis spp., Blissus spp., Calocoris spp., Campylomma livida, Cavelerius spp., Cimex spp., Creontiades dilutus, Dasynus piperis, Dichelops furcatus, Diconocoris hewetti, Dysdercus spp., Euschistus spp., Eurygaster spp., Heliopeltis spp., Horcias nobilellus, Leptocorisa spp., Leptoglossus phyllopus, Lygus spp., Macropes excavatus, Miridae, Nezara spp., Oebalus spp., Pentomidae, Piesma quadrata, Piezodorus spp., Psallus seriatus, Pseudacysta persea, Rhodnius spp., Sahlbergella singularis, Scotinophora spp., Stephanitis nashi, Tibraca spp., Triatoma spp.; from the order of the Homoptera, for example, Acyrthosipon spp., Aeneolamia spp., Agonoscena spp., Aleurodes spp., Aleurolobus barodensis, Aleurothrixus spp., Amrasca spp., Anuraphis cardui, Aonidiella spp., Aphanostigma piri, Aphis spp., Arboridia apicalis, Aspidiella spp., Aspidiotus spp., Atanus spp., Aulacorthum solani, Bemisia spp., Brachycaudus helichrysii, Brachycolus spp., Brevicoryne brassicae, Calligypona marginata, Carneocephala fulgida, Ceratovacuna lanigera, Cercopidae, Ceroplastes spp., Chaetosiphon fragaefolii, Chionaspis tegalensis, Chlorita onukii, Chromaphis juglandicola, Chrysomphalus ficus, Cicadulina mbila, Coccomytilus halli, Coccus spp., Cryptomyzus ribis, Dalbulus spp., Dialeurodes spp., Diaphorina spp., Diaspis spp., Doralis spp., Drosicha spp., Dysaphis spp., Dysmicoccus spp., Empoasca spp., Eriosoma spp., Erythroneura spp., Euscelis bilobatus, Geococcus coffeae, Homalodisca coagulata, Hyalopterus arundinis, Icerya spp., Idiocerus spp., Idioscopus spp., Laodelphax striatellus, Lecanium spp., Lepidosaphes spp., Lipaphis erysimi, Macrosiphum spp., Mahanarva fimbriolata, Melanaphis sacchari, Metcalfiella spp., Metopolophium dirhodum, Monellia costalis, Monelliopsis pecanis, Myzus spp., Nasonovia ribisnigri, Nephotettix spp., Nilaparvata lugens, Oncometopia spp., Orthezia praelonga, Parabemisia myricae, Paratrioza spp., Parlatoria spp., Pemphigus spp., Peregrinus maidis, Phenacoccus spp., Phloeomyzus passerinii, Phorodon humuli, Phylloxera spp., Pinnaspis aspidistrae, Planococcus spp., Protopulvinaria pyriformis, Pseudaulacaspis pentagona, Pseudococcus spp., Psylla spp., Pteromalus spp., Pyrilla spp., Quadraspidiotus spp., Quesada gigas, Rastrococcus spp., Rhopalosiphum spp., Saissetia spp., Scaphoides titanus, Schizaphis graminum, Selenaspidus anticulatus, Sogata spp., Sogatella furcifera, Sogatodes spp., Stictocephala fes-

*tina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*; from the order of the Hymenoptera, for example, Diprion spp., *Hoplocampa* spp., *Lasius* spp., *Mono-morium pharaonis, Vespa* spp.; from the order of the Isopoda, for example, *Armadillidium vulgare, Oniscus asellus, Porcellio scaber*; from the order of the Isoptera, for example, *Reticulitermes* spp., *Odontotermes* spp.; from the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.; from the order of the Orthoptera, for example, *Acheta domesticus, Blatta onientalis, Blattella germanica, Gryllotalpa* spp., *Leucophaea maderae, Locusta* spp., *Melanoplus* spp., *Periplaneta americana, Schistocerca gregaria*; from the order of the Siphonaptera, for example, *Ceratophyllus* spp., *Xenopsylla cheopis*. From the order of the Symphyla, for example, *Scutigerella immaculata*; from the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.; from the order of the Thysanura, for example, *Lepisma saccharina*. The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The combinations according to the present invention are furthermore particularly effective against the following pests: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta_migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compound of formula I and mixtures of the invention may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The mixtures of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and pulses.

The mixtures of the invention may be used on soybean to control, for example, *Elasmopalpus lignosellus, Diloboderus abderus, Diabrotica speciosa, Sternechus subsignatus, Formicidae, Agrotis ypsilon, Julus* spp., *Anticarsia gemmatalis, Megascelis* ssp., *Procornitermes* ssp., *Gryllotalpidae, Nezara viridula, Piezodorus* spp., *Acrosternum* spp., *Neomegalotomus* spp., *Cerotoma trifurcata, Popillia japonica, Edessa* spp., *Liogenys fuscus, Euchistus heros, stalk borer, Scaptocoris castanea, phyllophaga* spp., *Pseudoplusia includens, Spodoptera* spp., *Bemisia tabaci, Agriotes* spp. The mixtures of the invention are preferably used on soybean to control *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Scaptocoris castanea, Agriotes* spp.

The mixtures of the invention may be used on corn to control, for example, *Euchistus heros, Dichelops furcatus, Diloboderus abderus, Elasmopalpus lignosellus, Spodoptera frugiperda, Nezara viridula, Cerotoma trifurcata, Popillia japonica, Agrotis ypsilon, Diabrotica speciosa, Heteroptera, Procornitermes* ssp., *Scaptocoris castanea, Formicidae, Julus* ssp., *Dalbulus maidis, Diabrotica virgifera, Mocis latipes, Bemisia tabaci, heliothis* spp., *Tetranychus* spp., *thrips* spp., *phyllophaga* spp., *scaptocoris* spp., *Liogenys fuscus, Spodoptera* spp., *Ostrinia* spp., *Sesamia* spp., *Agriotes* spp. The mixtures of the invention are preferably used on corn to control *Euchistus heros, Dichelops furcatus, Diloboderus abderus, Nezara viridula, Cerotoma trifurcata, Popillia japonica, Diabrotica speciosa, Diabrotica virgifera, Tetranychus* spp., *thrips* spp., *phyllophaga* spp., *scaptocoris* spp., *Agriotes* spp.

The mixtures of the invention may be used on sugar cane to control, for example, *Sphenophorus* spp., termites, *Mahanarva* spp. The mixtures of the invention are preferably used on sugar cane to control termites, *Mahanarva* spp.

The mixtures of the invention may be used on alfalfa to control, for example, *Hypera brunneipennis, Hypera postica, Colias eurytheme, Collops* spp., *Empoasca solana, Epitrix, Geocoris* spp., *Lygus hesperus, Lygus lineolaris, Spissistilus* spp., *Spodoptera* spp., *Trichoplusia ni*. The mixtures of the invention are preferably used on alfalfa to control *Hypera brunneipennis, Hypera postica, Empoasca solana, Epitrix, Lygus hesperus, Lygus lineolaris, Trichoplusia ni*.

The mixtures of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca solana, thrips* spp., *Spodoptera* spp., *Delia* spp. The mixtures of the invention are preferably used on brassicas to control *Plutella xylostella Pieris* spp., *Plusia* spp., *Trichoplusia ni, Phyllotreta* spp., *thrips* spp.

The mixtures of the invention may be used on oil seed rape, e.g. canola, to control, for example, *Meligethes* spp., *Ceutorhynchus napi, Psylloides* spp.

The mixtures of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp. The mixtures of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp.

The mixtures of the invention may be used on cotton to control, for example, *Anthonomus grandis, Pectinophora* spp., *heliothis* spp., *Spodoptera* spp., *Tetranychus* spp., *Empoasca* spp., *thrips* spp., *Bemisia tabaci, Lygus* spp., *phyllophaga* spp., *Scaptocoris* spp. *Austroasca viridigrisea, Creontiades* spp., *Oxycaraenus hyalinipennis, Dysdercus cingulatus*. The mixtures of the invention are preferably used on cotton to control *Anthonomus grandis, Tetranychus* spp., *Empoasca* spp., *thrips* spp., *Lygus* spp., *phyllophaga* spp., *Scaptocoris* spp. *Austroasca viridigrisea, Creontiades* spp., *Oxycaraenus hyalinipennis, Dysdercus cingulatus*.

The mixtures of the invention may be used on rice to control, for example, *Leptocorisa* spp., *Cnaphalocrosis* spp., *Chilo* spp., *Scirpophaga* spp., *Lissorhoptrus* spp., *Oebalus pugnax*. The mixtures of the invention are preferably used on rice to control *Leptocorisa* spp., *Lissorhoptrus* spp., *Oebalus pugnax*.

The mixtures of the invention may be used on coffee to control, for example, *Hypothenemus Hampei, Perileucoptera Coffeella, Tetranychus* spp., *Brevipalpus* spp. The mixtures of the invention are preferably used on coffee to control *Hypothenemus Hampei, Brevipalpus* spp., *Perileucoptera Coffeella*.

The mixtures of the invention may be used on citrus to control, for example, *Panonychus citri, Phyllocoptruta oleivora, Brevipalpus* spp., *Diaphorina citri, Scirtothrips* spp., *thrips* spp., *Unaspis* spp., *Ceratitis capitata, Phyllocnistis* spp. The mixtures of the invention are preferably used on citrus to control *Panonychus citri, Phyllocoptruta oleivora, Brevipalpus* spp., *Diaphorina citri, Scirtothrips* spp., *thrips* spp., *Phyllocnistis* spp.

The mixtures of the invention may be used on almonds to control, for example, *Amyelois transitella, Tetranychus* spp.

The mixtures of the invention may be used on fruiting vegetable, including tomatoes, pepper, chili, eggplant, cucumber, squash, pulses etc, to control *thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., *Paratrioza* spp., *Frankliniella occidentalis, Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. *Maruca* spp. The mixtures of the invention are preferably used on fruiting vegetable, including tomatoes, pepper, chili, eggplant, cucumber, squash, pulses etc, to control, for example, *thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp. *Maruca* spp.

The mixtures of the invention may be used on tea to control, for example, *Pseudaulacaspis* spp., *Empoasca* spp., *Scirtothrips* spp., *Caloptilia theivora*. The mixtures of the invention are preferably used on tea to control *Empoasca* spp., *Scirtothrips* spp.

The mixtures of the invention may be used on bulb vegetables, including onion, leek etc to control, for example, *thrips* spp., *Spodoptera* spp., *heliothis* spp. The mixtures of the invention are preferably used on bulb vegetables, including onion, leek etc to control *thrips* spp.

The mixtures of the invention may be used on grapes to control, for example, *Empoasca* spp., *Lobesia* spp., *Frankliniella* spp., *thrips* spp., *Tetranychus* spp., *Rhipiphorothrips Cruentatus, Eotetranychus Willamettei, Erythroneura Elegantula, Scaphoides* spp. *Scelodonta strigicollis*. The mixtures of the invention are preferably used on grapes to control *Frankliniella* spp., *thrips* spp., *Tetranychus* spp., *Rhipiphorothrips Cruentatus, Scaphoides* spp. *Scelodonta strigicollis*.

The mixtures of the invention may be used on pome fruit, including apples, pairs etc, to control, for example, *Cacopsylla* spp., *Psylla* spp., *Panonychus ulmi, Cydia pomonella*. The mixtures of the invention are preferably used on pome fruit, including apples, pairs etc, to control *Cacopsylla* spp., *Psylla* spp., *Panonychus ulmi*.

The mixtures of the invention may be used on stone fruit to control, for example, *Grapholita molesta, Scirtothrips* spp., *thrips* spp., *Frankliniella* spp., *Tetranychus* spp. The mixtures of the invention are preferably used on stone fruit to control *Scirtothrips* spp., *thrips* spp., *Frankliniella* spp., *Tetranychus* spp.

In another embodiment compounds of formula I and mixtures of the invention may be used on rice to control *Baliothrips biformis* (Thrips), *Chilo* spp. (e.g. *Chilo polychrysus* (Dark headed striped borer), *Chilo suppressalis*

(Rice stemborer), *Chilo indicus* (Paddy stem borer), *Chilo polychrysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema oryzae* (Rice leafbeetle), *Leptocorsia acuta* (Rice bug), *Leptocorsia oratorius* (rice bug), *Lissorhoptrus oryzophilus* (rice water weevil), *Mythemina separata* (armyworm), *Nephottetix* spp. (Green leafhopper) (e.g. *Nephotettix cincticeps, Nephotettix malayanus, Nephotettix nigropictus, Nephotettix parvus, Nephottetix virescens*), *Nilaparvata lugens* (Brown Planthopper), *Nymphula depunctalis* (Rice caseworm), *Orseolia oryzae* (Rice Gall midge), *Oulema oryzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki*.

The compounds of formula I and mixtures of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of formula I and mixtures of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, *Thrips*, Tip moths, Tussock moth larvae, Wasps, Broadmites, Brown softscales, California redscales (crawlers), Clover mites, Mealybugs, Pineneedlescales (crawlers), Spider mites, Whiteflies.

The compounds of formula I and mixtures of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The mixtures of the invention, in particular those in the tables above, may be used for soil applications, including as a seed application, to target at least the following: sucking pests such as aphids, *thrips*, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on *lepidoptera*, such as *spodoptera*, cutworms, *elasmoplpus, plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. oncorn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The mixtures of the invention, in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp *Hipnodes bicolor; Ctenicera destructor; Limonius canu; Limonius californicus*; rice water weevil: *Lissorhoptrus oryzophilus*; Red Legged earth mites: *Halotydeus destructor*.

For soil applications using compounds of formula I on sugar cane, including application on sugar cane propogation material such as buds, the following mixing partners are of particular interest: insecticides selected from neonicotinoids, in particular thiamethoxam, imidacloprid and clothianidin, sulfoxaflor, abamectin, carbofuran, tefluthrin, fipronil, ethiprole, spinosad, lamda-cyhalothrin, bisamides, in particular chlorantraniliprole, cyantraniliprole, flubendiamide; optionally with fungicides selected from azoxystrobin, cyproconazole, thiabendazole, fluazinam, fludioxonil, mefenoxam, Sedaxane. For foliar applications using compounds of formula I on sugar cane, the following mixing partners are of particular interest: insecticides selected from thiamethoxam, Lambda cyhalothrin, spirotetramat, spinetoran, chlorantraniliprole, lufenuron; optionally with fungicides selected from N-[9-(dichloromethylene)-1,2,3,4-tetrahydro-1,4-methanonaphthalen-5-yl]-3-(difluoromethyl)-1-methyl-1H-pyrazole-4-carboxamide [CAS 1072957-71-1], azoxystrobin, cyproconazole, protioconazole. Combinations with glyphosate are also of interest.

Particular combinations of interest for sugar cane, particularly on sugar cane propogation material such as buds, include a compound of formula I with thiamethoxam and abamectin, a compound of formula I with thiamethoxam and cyantraniliprole, a compound of formula I with thiamethoxam and chlorantraniliprole. Further combinations of particular interest for sugar cane include a compound of formula I+thiamethoxam+abamectin+mefenoxam+fludioxonil+azoxystrobin+thiabendazole; a compound of formula I+abamectin+mefenoxam+fludioxonil+azoxystrobin+thiabendazole, a compound of formula I+thiamethoxam+mefenoxam+fludioxonil+azoxystrobin+thiabendazole, a compound of formula I+thiamethoxam+abamectin+mefenoxam+fludioxonil+azoxystrobin+thiabendazole, a compound of formula I+thiamethoxam+abamectin+fludioxonil+azoxystrobin+thiabendazole, a compound of formula I+thiamethoxam+abamectin+mefenoxam+azoxystrobin+thiabendazole, a compound of formula I+thiamethoxam+abamectin+mefenoxam+fludioxonil+thiabendazole, a compound of formula I+thiamethoxam+abamectin+mefenoxam+fludioxonil+azoxystrobin. Example of ratios are below.

The amount of a combination of the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of pest to be controlled or the application time.

The mixtures comprising a compound of formula I, e.g. those selected from table A, and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from table A and the active ingredients as described above is not essential for working the present invention.

The synergistic activity of the combination is apparent from the fact that the pesticidal activity of the composition of A+B is greater than the sum of the pesticidal activities of A and B.

The method of the invention comprises applying to the useful plants, the locus thereof or propagation material thereof in admixture or separately, a synergistically effective aggregate amount of a component A and a component B.

Some of said combinations according to the invention have a systemic action and can be used as foliar, soil and seed treatment pesticides.

With the combinations according to the invention it is possible to inhibit or destroy the pests which occur in plants or in parts of plants (fruit, blossoms, leaves, stems, tubers, roots) in different useful plants, while at the same time the parts of plants which grow later are also protected from attack by pests.

The compound of formula I are understood to represent a new mode of action. Accordingly, it may be noted that compounds of formula I may be used to control acarides, insects and nematodes, preferably insects, that are resistant to active ingredients having other modes of action, e.g. it may be included in resistant management programs.

The combinations of the present invention are of particular interest for controlling pests in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The combinations according to the invention are applied by treating the pests, the useful plants, the locus thereof, the propagation material thereof, the natural substances of plant and/or animal origin, which have been taken from the natural life cycle, and/or their processed forms, or the industrial materials threatened by pests, attack with a combination of components A and B in a synergistically effective amount.

The combinations according to the invention may be applied before or after infection or contamination of the useful plants, the propagation material thereof, the natural substances of plant and/or animal origin, which have been taken from the natural life cycle, and/or their processed forms, or the industrial materials by the pests.

The combinations according to the invention can be used for controlling, i. e. containing or destroying, pests of the abovementioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these pests.

When applied to the useful plants the compound of formula I is generally applied at a rate of 1 to 500 g a.i./ha in association with 1 to 2000 g a.i./ha, of a compound of component B, depending on the class of chemical employed as component B.

Generally for plant propagation material, such as seed treatment, application rates can vary from 0.001 to 10 g/kg of seeds of active ingredients. When the combinations of the present invention are used for treating seed, rates of 0.001 to 5 g of a compound of formula I per kg of seed, preferably from 0.01 to 1 g per kg of seed, and 0.001 to 5 g of a compound of component B, per kg of seed, preferably from 0.01 to 1 g per kg of seed, are generally sufficient.

The weight ratio of A to B may generally be between 1000:1 and 1:1000. In other embodiments that weight ratio of A to B may be between 500:1 to 1:500, for example between 100:1 to 1:100, for example between 1:50 to 50:1, for example 1:20 to 20:1. Other embodiments of weight ratios of component (B) to component (A) range from 500:1 to 1:250, with one embodiment being from 200:1 to 1:150, another embodiment being from 150:1 to 1:50 and another embodiment being from 50:1 to 1:10. Also of note are weight ratios of component (B) to component (A) which range from 450:1 to 1:300, with one embodiment being from 150:1 to 1:100, another embodiment being from 30:1 to 1:25 and another embodiment being from 10:1 to 1:10. Other embodiments include 1:5 to 5:1, for example 4:1, 3:1, 2:1, 1:1, 1:2, 1:3, 1:4, 1:5.

The invention also provides pesticidal mixtures comprising a combination of components A and B as mentioned above in a synergistically effective amount, together with an agriculturally acceptable carrier, and optionally a surfactant.

*Spodoptera* preferably means *Spodoptera littoralis*. *Heliothis* preferably means *Heliothis virescens*. *Tetranychus* preferably means *Tetranychus urticae*.

The compositions of the invention may be employed in any conventional form, for example in the form of a twin pack, a powder for dry seed treatment (DS), an emulsion for seed treatment (ES), a flowable concentrate for seed treatment (FS) (e.g. with high active ingredient concentration), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspoemulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

The rates of application of a plant propagation material treatment varies, for example, according to type of use, type of crop, the specific compound(s) and/or agent(s) used, and type of plant propagation material. The suitable rate is an effective amount to provide the desired action (such as disease or pest control) and can be determined by trials and routine experimentation known to one of ordinary skill in the art.

Generally for soil treatments, application rates can vary from 0.05 to 3 kg per hectare (g/ha) of ingredients. Generally for seed treatments, application rates can vary from 0.5 to 1000 g/100 kg of seeds of ingredients.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with a compound of component B, and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

FORMULATION EXAMPLES

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |

| Powders for dry seed treatment | a) | b) | c) |
|---|---|---|---|
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, seeds can be treated and protected against infestation by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, seeds can be treated and protected against infestation by spraying, pouring or immersion.

The invention further pertains to a product for use in agriculture or horticulture comprising a capsule wherein at least a seed treated with the inventive compound is located. In another embodiment, the product comprises a capsule wherein at least a treated or untreated seed and the inventive compound are located.

Slow Release Capsule Suspension 28 parts of the inventive compound are mixed with 2 parts of an aromatic solvent and 7 parts of toluene diisocyanate/polymethylene-polyphenylisocyanate-mixture (8:1). This mixture is emulsified in a mixture of 1.2 parts of polyvinyl-alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredient. The medium capsule diameter is 8-15 microns. The resulting formulation is applied to seeds as an aqueous suspension in a suitable apparatus.

EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of $\geq 1.2$ indicates significant improvement over the purely complementary addition of activities (expected activity), while an SF of $\leq 0.9$ in the practical application routine signals a loss of activity compared to the expected activity.

Tables A, B and C show mixtures of the present invention demonstrating notable synergistic effects. As the percent of mortality cannot exceed 100 percent, the unexpected increase in insecticidal activity can be greatest only when the separate active ingredient components alone are at application rates providing considerably less than 100 percent control. Synergy may not be evident at low application rates where the individual active ingredient components alone have little activity. However, in some instances high activity was observed for combinations wherein individual active ingredient alone at the same application rate had essentially no activity. The synergism is remarkable.

*Heliothis virescens* (Tobacco Budworm)

Eggs (0-24 h old) are placed in 24-well microtiter plate on artificial diet and treated with test solutions (DMSO) by pipetting. After an incubation period of 4 days, samples are checked for larval mortality.

TABLE A

|  | Application ppm | 1-1 + SPAT observed control % | 1-1 observed control % | SPAT observed control % | expected control % | difference |
|---|---|---|---|---|---|---|
| 1-1 + SPAT | 25 + 25 | 90 | 90 | 0 | 90 | 0 |
| 1-1 + SPAT | 12.5 + 12.5 | 90 | 85 | 0 | 85 | +5 |
| 1-1 + SPAT | 6.25 + 6.25 | 80 | 85 | 0 | 85 | −5 |
| 1-1 + SPAT | 3.125 + 3.125 | 80 | 45 | 0 | 45 | +35 |
| 1-1 + SPAT | 1.56 + 1.56 | 35 | 0 | 0 | 0 | +35 |
| 1-1 + SPAT | 25 + 50 | 90 | 90 | 0 | 90 | 0 |
| 1-1 + SPAT | 12.5 + 25 | 90 | 85 | 0 | 85 | +5 |
| 1-1 + SPAT | 6.25 + 12.5 | 90 | 85 | 0 | 85 | +5 |
| 1-1 + SPAT | 3.125 + 6.25 | 80 | 45 | 0 | 45 | +35 |
| 1-1 + SPAT | 1.56 + 3.12 | 65 | 0 | 0 | 0 | +65 |
| 1-1 + SPAT | 0.78 + 1.56 | 25 | 0 | 0 | 0 | +25 |
| 1-1 + SPAT | 12.5 + 50 | 85 | 85 | 0 | 85 | 0 |
| 1-1 + SPAT | 6.25 + 25 | 85 | 85 | 0 | 85 | 0 |
| 1-1 + SPAT | 3.125 + 12.5 | 80 | 45 | 0 | 45 | +35 |
| 1-1 + SPAT | 1.56 + 6.25 | 70 | 0 | 0 | 0 | +70 |
| 1-1 + SPAT | 0.78 + 3.12 | 25 | 0 | 0 | 0 | +25 |
| 1-1 + SPAT | 12.5 + 100 | 90 | 85 | 0 | 85 | +5 |
| 1-1 + SPAT | 6.25 + 50 | 75 | 85 | 0 | 85 | −10 |
| 1-1 + SPAT | 3.125 + 25 | 70 | 45 | 0 | 45 | +25 |
| 1-1 + SPAT | 1.56 + 12.5 | 50 | 0 | 0 | 0 | +50 |
| 1-1 + SPAT | 0.78 + 6.25 | 25 | 0 | 0 | 0 | +25 |
| 1-1 + SPAT | 12.5 + 200 | 90 | 85 | 60 | 94 | −4 |
| 1-1 + SPAT | 6.25 + 100 | 80 | 85 | 0 | 85 | −5 |
| 1-1 + SPAT | 3.125 + 50 | 75 | 45 | 0 | 45 | +30 |
| 1-1 + SPAT | 1.56 + 25 | 85 | 0 | 0 | 0 | +85 |
| 1-1 + SPAT | 0.78 + 12.5 | 25 | 0 | 0 | 0 | +25 |

TABLE B

| | Application ppm | 2-7 + DMET observed control % | 2-7 Observe control % | DMET observed control % | expected control % | difference |
|---|---|---|---|---|---|---|
| 2-7 + DMET | 0.4 + 0.1 | 90 | 90 | 0 | 90 | 0 |
| 2-7 + DMET | 0.2 + 0.05 | 90 | 80 | 0 | 80 | +10 |
| 2-7 + DMET | 0.1 + 0.025 | 70 | 55 | 0 | 55 | +15 |
| 2-7 + DMET | 0.05 + 0.0125 | 0 | 10 | 0 | 10 | −10 |
| 2-7 + DMET | 0.4 + 0.2 | 90 | 90 | 0 | 90 | 0 |
| 2-7 + DMET | 0.2 + 0.1 | 85 | 80 | 0 | 80 | +5 |
| 2-7 + DMET | 0.1 + 0.05 | 70 | 55 | 0 | 55 | +15 |
| 2-7 + DMET | 0.05 + 0.025 | 50 | 10 | 0 | 10 | +40 |
| 2-7 + DMET | 0.2 + 0.2 | 90 | 80 | 0 | 80 | +10 |
| 2-7 + DMET | 0.1 + 0.1 | 75 | 55 | 0 | 55 | +20 |
| 2-7 + DMET | 0.05 + 0.05 | 75 | 10 | 0 | 10 | +65 |
| 2-7 + DMET | 0.2 + 0.4 | 90 | 80 | 0 | 80 | +10 |
| 2-7 + DMET | 0.1 + 0.2 | 75 | 55 | 0 | 55 | +20 |
| 2-7 + DMET | 0.05 + 0.1 | 40 | 10 | 0 | 10 | +30 |
| 2-7 + DMET | 0.2 + 0.8 | 90 | 80 | 0 | 80 | +10 |
| 2-7 + DMET | 0.1 + 0.4 | 70 | 55 | 0 | 55 | +15 |
| 2-7 + DMET | 0.05 + 0.2 | 45 | 10 | 0 | 10 | +35 |
| 2-7 + DMET | 0.025 + 0.1 | 50 | 0 | 0 | 0 | +50 |

*Tetranychus urticae* (Two-Spotted Spider Mite)

Bean leaf discs on agar in 24-well microtiter plates are sprayed with test solutions (DMSO). After drying, the leaf discs are infested with mite populations of mixed ages. 8 days later, discs are checked for mixed population mortality.

TABLE C

| | Application ppm | 2-7 + SPAT observed control % | 2-7 observed control % | SPAT observed control % | expected control % | difference |
|---|---|---|---|---|---|---|
| 2-7 + SPAT | 3.0 + 12.5 | 100 | 80 | 65 | 93 | +7 |
| 2-7 + SPAT | 0.75 + 3.125 | 65 | 25 | 0 | 25 | +40 |
| 2-7 + SPAT | 0.375 + 1.56 | 50 | 0 | 0 | 0 | +50 |
| 2-7 + SPAT | 3.0 + 25 | 100 | 80 | 80 | 96 | +4 |
| 2-7 + SPAT | 1.5 + 12.5 | 90 | 75 | 65 | 91.25 | −1.25 |
| 2-7 + SPAT | 0.375 + 3.125 | 20 | 0 | 0 | 0 | +20 |
| 2-7 + SPAT | 3.0 + 50 | 100 | 80 | 85 | 97 | +3 |
| 2-7 + SPAT | 1.5 + 25 | 100 | 75 | 80 | 95 | +5 |
| 2-7 + SPAT | 3.0 + 100 | 95 | 80 | 85 | 97 | −2 |
| 2-7 + SPAT | 1.5 + 50 | 100 | 75 | 85 | 96.25 | +3.75 |
| 2-7 + SPAT | 0.375 + 12.5 | 90 | 0 | 65 | 65 | +25 |
| 2-7 + SPAT | 3.0 + 200 | 100 | 80 | 85 | 97 | +3 |
| 2-7 + SPAT | 1.5 + 100 | 100 | 75 | 85 | 96.25 | +3.75 |
| 2-7 + SPAT | 0.375 + 25 | 90 | 0 | 80 | 80 | +10 |
| 2-7 + SPAT | 0.187 + 12.5 | 55 | 0 | 65 | 65 | −10 |

In the above tables column 2 shows the application rates used, where the first rate given corresponds to the compound in column 4 and the second rate given corresponds to the compound in column 5 Columns 4 and 5 show the control observed from the compounds alone. Column 3 shows the control observed from the combined application of both compounds. Data is not shown for experiments where there was no insect mortality when the compounds were applied alone and in combination, or where one compound alone and the combination both resulted in complete mortality. When a compound applied alone gave no control at a particular rate, it is assumed that lower rates of that compound alone also give no control. DMET=deltamethrin, SPAT=spirotetramat, 1-1 is compound 1 in Table 1, 2-7 is compound 7 in Table 2.

The invention claimed is:

1. A pesticidal mixture comprising a component A and a component B, wherein component A is a compound of formula IA

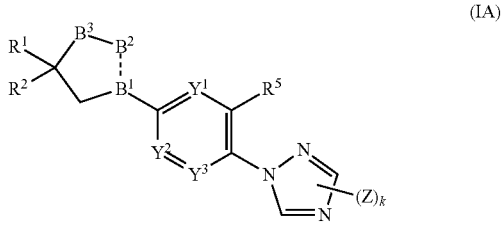

wherein

—$B^1$—$B^2$—$B^3$— is —C=N—O— or —C=N—$CH_2$—;

$R^1$ is trifluoromethyl;

$R^2$ is 3,5-dichlorophenyl or 3,4,5-trichlorophenyl;

$Y^1$ is CH;

$Y^2$ and $Y^3$ are each CH;

$R^5$ is hydrogen, cyano, chloro, bromo, fluoro, methyl, or trifluoromethyl; and k is 0;

and component B is a compound selected from a) deltamethrin; and q) spirotetramat.

2. A pesticidal mixture according to claim 1, wherein —$B^1$—$B^2$—$B^3$— is —C=N—O—.

3. A pesticidal mixture according to claim 1, wherein —$B^1$—$B^2$—$B^3$— is —C=N—$CH_2$—.

4. A pesticidal mixture according to claim 1, wherein component B is spirotetramat.

5. A pesticidal mixture according to claim 1, wherein component B is deltamethrin.

6. A pesticidal mixture according to claim 1, wherein the weight ratio of A to B is 1000:1 to 1:1000.

7. A pesticidal mixture according to claim 1 wherein component B is spirotetramat, wherein, optionally, the weight ratio of A to B is 1:25 to 25:1.

8. A pesticidal mixture according to claim 3 wherein component B is spirotetramat or deltamethrin, wherein, optionally, the weight ratio of A to B is 1:25 to 25:1.

9. A method of controlling insects, acarines, nematodes or molluscs which comprises applying to a pest, to a locus of a pest, or to a plant susceptible to attack by a pest a combination of components A and B, wherein components A and B are as defined in claim 1.

* * * * *